United States Patent
Boyes et al.

(10) Patent No.: US 11,857,719 B2
(45) Date of Patent: Jan. 2, 2024

(54) FILTER ASSEMBLY

(71) Applicant: Fisher & Paykel Healthcare Limited, Auckland (NZ)

(72) Inventors: Richard John Boyes, Auckland (NZ); Christian Francis Fischer, Auckland (NZ); Ali Ghalib Abdul Rahman Ghalib, Auckland (NZ); Jessica Kristen Sloane, Auckland (NZ); Monika Baumann, Auckland (NZ); Bernard Tsz Lun Ip, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 748 days.

(21) Appl. No.: 16/466,913

(22) PCT Filed: Dec. 8, 2017

(86) PCT No.: PCT/NZ2017/050159
§ 371 (c)(1),
(2) Date: Jun. 5, 2019

(87) PCT Pub. No.: WO2018/106127
PCT Pub. Date: Jun. 14, 2018

(65) Prior Publication Data
US 2019/0344023 A1  Nov. 14, 2019

Related U.S. Application Data

(60) Provisional application No. 62/432,422, filed on Dec. 9, 2016.

(51) Int. Cl.
*A61M 13/00* (2006.01)
*A61M 16/10* (2006.01)
(Continued)

(52) U.S. Cl.
CPC ...... *A61M 13/003* (2013.01); *A61M 16/0875* (2013.01); *A61M 16/106* (2014.02);
(Continued)

(58) Field of Classification Search
CPC .. A61M 13/003; A61M 16/16; A61M 16/109; A61M 2205/75; A61M 16/0808;
(Continued)

(56) References Cited

U.S. PATENT DOCUMENTS

| 4,727,871 A | 3/1988 | Smargiassi et al. |
| 5,143,060 A | 9/1992 | Smith |

(Continued)

FOREIGN PATENT DOCUMENTS

| GB | 1294307 | 10/1972 |
| GB | 2277689 | 11/1994 |

(Continued)

OTHER PUBLICATIONS

Supplementary European Search Report for Application No. EP 17 87 9155 dated Jun. 12, 2020.
(Continued)

*Primary Examiner* — Amber R Stiles
*Assistant Examiner* — Phoebe Anne Staton
(74) *Attorney, Agent, or Firm* — Knobbe Martens Olson & Bear LLP

(57) ABSTRACT

In one embodiment, a filter assembly for use in an insufflation system is described. The filter assembly comprises: a filter medium operative to filter medical gases; a housing comprising an inlet, an outlet and the filter medium, the housing defining a gases flow path through the filter medium between the inlet and the outlet; and at least one heating element being positioned in the housing and being configured to heat the filter medium; and wherein, the at least one heating element is spaced apart from the filter medium and from an inner surface of the housing.

19 Claims, 20 Drawing Sheets

(51) Int. Cl.
*A61M 16/16* (2006.01)
*A61M 16/08* (2006.01)

(52) U.S. Cl.
CPC ...... *A61M 16/1095* (2014.02); *A61M 16/161* (2014.02); *A61M 2202/0225* (2013.01); *A61M 2205/3327* (2013.01); *A61M 2205/3331* (2013.01); *A61M 2205/3334* (2013.01); *A61M 2205/3368* (2013.01); *A61M 2205/3569* (2013.01); *A61M 2205/3653* (2013.01); *A61M 2205/7527* (2013.01); *A61M 2205/7536* (2013.01)

(58) Field of Classification Search
CPC ...... A61M 16/1085; A61M 2210/1021; A61M 2202/02; A61M 2205/7536; A61M 13/00; A61M 2205/3327; A61M 2205/3331; A61M 2205/3334; A61M 2205/3368; A61M 2205/3653; A61M 2205/7527; A61M 16/161; A61M 16/0875; A61M 2202/0225; A61M 2205/3569
See application file for complete search history.

(56) References Cited

U.S. PATENT DOCUMENTS

| | | | |
|---|---|---|---|
| 7,497,215 B1 | 3/2009 | Nguyen et al. | |
| 2004/0102731 A1* | 5/2004 | Blackhurst | A61B 1/00154 604/113 |
| 2006/0118113 A1* | 6/2006 | Bremner | A61M 16/16 128/204.22 |
| 2010/0206308 A1* | 8/2010 | Klasek | A61M 16/108 128/203.26 |
| 2011/0126836 A1 | 6/2011 | Winter et al. | |
| 2013/0098360 A1 | 4/2013 | Humez et al. | |
| 2013/0152929 A1* | 6/2013 | Stenzler | A61M 16/1095 128/205.12 |
| 2013/0233318 A1 | 9/2013 | Graham et al. | |
| 2016/0001032 A1* | 1/2016 | Drew | A61M 16/0875 128/204.17 |
| 2018/0311459 A1* | 11/2018 | Winkler | A61M 16/0003 |

FOREIGN PATENT DOCUMENTS

| | | |
|---|---|---|
| WO | WO 1991/001771 | 2/1991 |
| WO | WO 1996/032154 | 10/1996 |
| WO | WO 1999/059661 | 11/1999 |
| WO | WO 2005/056091 | 6/2005 |
| WO | WO 2007/069922 | 6/2007 |
| WO | WO 2015/142192 | 9/2015 |
| WO | WO 2016/048172 | 3/2016 |
| WO | WO/2018/097738 | 5/2018 |

OTHER PUBLICATIONS

International Search Report for International Application No. PCT/NZ2017/050159 dated Apr. 11, 2018.

* cited by examiner

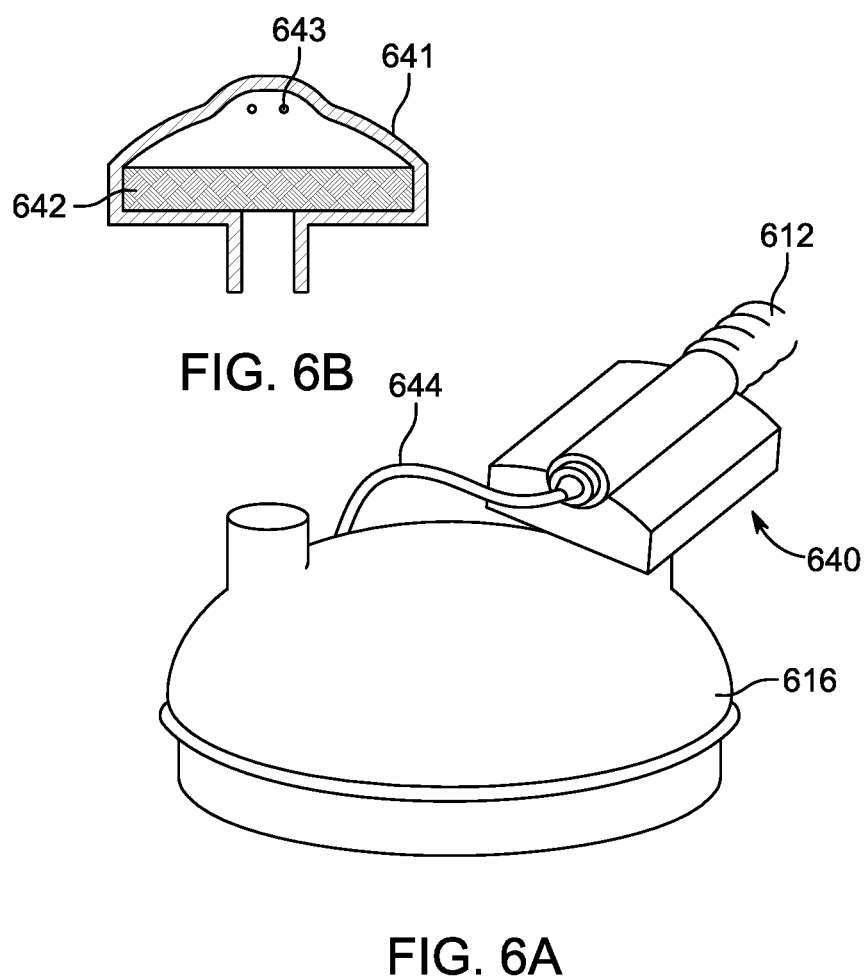

FILTER ASSEMBLY

BACKGROUND

1. Field of the Invention

The present invention generally relates to filters for medical devices. More specifically, the present invention relates to a filter assembly for use in insufflation systems.

2. Description of Related Art

Insufflation gases can be used in surgery for a variety of purposes. In open surgery, gas can be insufflated into a body cavity for de-airing, as in cardiac surgery. In laparoscopic surgery, the abdominal wall can be distended using gas to provide room for instrument insertion and tissue dissection. Insufflation systems used to carry out these surgical procedures generally comprise a gases source, a filter, a gas delivery circuit and a humidifier. The humidifier typically comprises a humidification chamber that holds a quantity of water. The humidifier generally includes a heater plate that heats the water to create a water vapour that is transmitted into the incoming gases to humidify the gases. The gases are transported out of the humidifier with the water vapour. The humidification chamber requires a minimum level of water to allow the humidification chamber to adequately humidify incoming gases. Accordingly, a health professional or person using the insufflation system needs to keep checking the water level in the humidification chamber and add more water when required.

Practitioners generally consider the filter to be dividing line between sterile and non-sterile portions of the system. Therefore, refilling or adding water may be a problem for traditional insufflation systems where the filter is positioned on the "dry-side" of the system (i.e. between the gases source and the humidifier) as this violates the integrity of the sterile portion of the system. On the other hand, moving the filter to the "wet-side" (i.e. between the humidifier and the patient) introduces the new problem of condensation building in the filter because of the humidified gases. The condensation may clog the filter, thereby reducing the gases flow rate through the filter.

It is an object of the invention to at least partially help to overcome these problems, or at least provide the public with a useful alternative.

SUMMARY

In a first aspect, the invention consists in a filter assembly for use in an insufflation system, the filter assembly including: a filter medium operative to filter medical gases; a housing comprising an inlet, an outlet and the filter medium, the housing defining a gases flow path through the filter medium between the inlet and the outlet; and at least one heating element being positioned in the housing and being configured to heat the filter medium; and wherein, the at least one heating element is spaced apart from the filter medium and from an inner surface of the housing.

In one embodiment, the insufflation system may comprise a humidification apparatus operative to humidify the medical gases for delivery to a patient, and the filter assembly may be positioned in use between the humidification apparatus and the patient. The said filter assembly may be positioned in use adjacent to a humidification chamber of the humidification apparatus. The at least one heating element may be positioned in the gases flow path between the inlet and the outlet of the housing. The at least one heating element may comprise one or more heater wires. The housing may be operative to be coupled to a patient conduit, the patient conduit being configured to deliver the humidified gases passing through the filter assembly to the patient. The at least one heating element may extend along the patient conduit.

In another embodiment, the filter assembly may further comprise at least one sensor positioned in the gases flow path between the inlet and the outlet of the housing. The sensor may be operative to measure data relevant to one or more of the following: a temperature; humidity; a pressure; and a flow rate of the gases flow. The data may be transmitted to the humidification apparatus or a remote apparatus via a wire or a flying lead. The data may be transmitted wirelessly to the humidification apparatus or a remote apparatus. The data may be transmitted by radio-frequency identification or Wi-Fi.

In a further embodiment, the inlet and/or the outlet of the housing may be operative to be coupled to a patient conduit. The filter assembly may further comprise a Luer connector operative to couple the inlet and/or the outlet to the patient conduit. The patient conduit may comprise heating wires configured to heat gases flowing through the patient conduit. The heating wires may be attached to or comprise the at least one heating element of the filter assembly.

In one embodiment, the filter medium may comprise one or more of the following: a membrane; a glass-based material, a hydrophobic material; paper; and a pleated material.

In a second aspect, the invention consists in a filter assembly for use in an insufflation system, the filter assembly including: a filter medium operative to filter humidified gases; a housing comprising an inlet, an outlet and the filter medium, the housing defining a gases flow path through the filter medium between the inlet and the outlet; and at least one heating element being positioned in the housing and being configured to heat the humidified gases flowing through the gases flow path; and wherein, the at least one heating element is positioned in the gases flow path downstream from the filter medium.

In one embodiment, the at least one heating element is spaced apart from the filter medium and from an inner surface of the housing.

In another embodiment, the at least one heating element may comprise one or more heater wires.

In a further embodiment, the outlet of the housing may be operative to be coupled to a patient conduit. The patient conduit may be permanently or removably attached to the outlet. The at least one heating element may be configured to extend along a length of the patient conduit.

In one embodiment, the filter assembly may further comprise an electrical power source coupling for supplying power to the at least one heating element.

In another embodiment, the filter assembly may be sterile.

In a further embodiment, the filter medium may comprise one or more of the following: a membrane; a glass-based material, a hydrophilic material; paper; and a pleated material. The filter medium may comprise parallel pleats. The filter medium may comprise a material at least partially composed of glass.

In one embodiment, the filter assembly may further comprise at least one sensor positioned the said gases flow path between the inlet and the outlet of the housing. The sensor may be operative to measure data relevant to one or more of the following: a temperature; humidity; a pressure; and a flow rate of the gases flow. The data may be transmitted to the humidification apparatus or a remote apparatus via a wire or a flying lead. The data may be transmitted wirelessly to the humidification apparatus or a remote apparatus. The data may be transmitted by radio-frequency identification or Wi-Fi.

In a third aspect, the invention consists in an elbow filter for use in an insufflation system, the elbow filter comprising: a filter medium operative to filter humidified gases; a housing comprising an inlet, an outlet and the filter medium, the housing defining a gases flow path through the filter medium between the inlet and the outlet; and wherein, the filter medium is positioned within the housing to span the inlet, and wherein the inlet and the outlet are oriented so that the housing form an elbow.

In one embodiment, the inlet may be operative to be coupled to an outlet port of a humidification apparatus, the outlet port extending substantially vertically from a humidification chamber of the humidification apparatus. The inlet of the housing may be configured so that condensate forming on a lower surface of the filter medium drains back to the humidification chamber.

In another embodiment, the outlet of the housing may be operative to be coupled to a patient conduit, the patient conduit being configured to deliver the humidified gases to a patient. The outlet may extend substantially horizontally from the housing of the elbow filter. The patient conduit may be permanently or removably attached to said outlet.

In a further embodiment, the housing may further comprise at least one heating element in the gases flow path downstream the filter medium. The at least one heating element may be spaced apart from the filter medium and from an inner surface of the housing. The at least one heating element may comprise one or more heater wires. The at least one element may be configured to extend along the patient conduit. The elbow filter may further comprise an electrical power source coupling for supplying power to the at least one heating element.

In one embodiment. the elbow filter may be sterile.

In another embodiment, the filter medium may comprise one or more of the following: a membrane; a glass-based material, a hydrophobic material; paper; and a pleated material. The filter medium may comprise parallel pleats. The filter medium may comprise a material at least partially composed of glass.

In a further embodiment, the filter assembly may further comprise at least one sensor positioned in the gases flow path between the inlet and the outlet of the housing. The sensor may be operative to measure data relevant to one or more of the following: a temperature; humidity; a pressure; and a flow rate of the gases flow. The data may be transmitted to the humidification apparatus or a remote apparatus via a wire or a flying lead. The data may be transmitted wirelessly to the humidification apparatus or a remote apparatus. The data may be transmitted by radio-frequency identification or Wi-Fi.

In a fourth aspect, the invention consists in a kit of parts for an unassembled insufflation system, the kit including: a delivery conduit configured to defined a gases flow path between a gases source and a patient interface; and a filter assembly comprising: a filter medium operative to filter medical gases; a housing comprising an inlet, an outlet and the filter medium, the housing defining a gases flow path through the filter medium between the inlet and the outlet; and at least one heating element being positioned in said housing and being configured to heat the filter medium; and wherein, the at least one heating element is spaced apart from the filter medium and an inner surface of the housing.

In one embodiment, the unassembled insufflation system may further comprise a humidification apparatus configured to be placed in the gases flow path between the gases source and the delivery conduit. The humidification apparatus may comprise a humidification chamber configured to hold a volume of liquid.

In another embodiment, the unassembled insufflation system may further comprise a supply conduit defining a gases flow path between the gases source and the humidification apparatus.

In a further embodiment, the filter assembly may comprise a delivery tube connector at a gases source end of the delivery tube.

In one embodiment, the filter assembly may comprise a delivery tube connector at a patient interface end of the delivery tube.

In a fifth aspect, the invention consists in a kit of parts for an unassembled insufflation system, the kit including: a delivery conduit configured to defined a gases flow path between a gases source and a patient interface; and a filter assembly comprising: a filter medium operative to filter humidified gases; a housing comprising an inlet, an outlet and the filter medium, the housing defining a gases flow path through the filter medium between the inlet and the outlet; and at least one heating element being positioned in the housing and being configured to heat the humidified gases flowing through the gases flow path; and wherein, the at least one heating element is positioned in the gases flow path downstream from the filter medium.

In one embodiment, the unassembled insufflation system may further comprise a supply conduit defining a gases flow path between the gases source and the humidification apparatus.

In another embodiment, the filter assembly may comprise a delivery tube connector at a gases source end of the delivery tube.

In a further embodiment, the filter assembly may comprise a delivery tube connector at a patient interface end of the delivery tube.

In a sixth aspect, the invention consists in a kit of parts for an unassembled insufflation system, the kit including: a delivery conduit configured to defined a gases flow path between a gases source and a patient interface; and an elbow filter comprising: a filter medium operative to filter humidified gases; a housing comprising an inlet, an outlet and the filter medium, the housing defining a gases flow path through the filter medium between the inlet and the outlet; and wherein, the filter medium is positioned within the housing to span the inlet, and wherein the inlet and the outlet are oriented so that the housing form an elbow.

In one embodiment, the unassembled insufflation system may further comprise a supply conduit defining a gases flow path between the gases source and the humidification apparatus.

In another embodiment, the filter assembly may comprise a delivery tube connector at a gases source end of the delivery tube.

In a further embodiment, the filter assembly may comprise a delivery tube connector at a patient interface end of the delivery tube.

In a seventh aspect, the invention consists in an insufflation system including: a gases source; a patient interface; a delivery conduit configured to defined a gases flow path between the gases source and the patient interface; and a filter assembly forming part of the gases flow path, the filter assembly comprising: a filter medium operative to filter medical gases; a housing comprising an inlet, an outlet and the filter medium, the housing defining a gases flow path through the filter medium between the inlet and the outlet; and at least one heating element being positioned in the housing and being configured to heat the filter medium; and wherein, the at least one heating element is spaced apart from the filter medium and an inner surface of the housing.

In one embodiment, the insufflation system may further comprise a humidification apparatus configured to be placed in the gases flow path between the gases source and the patient interface such that the delivery conduit defines the gases flow path between the humidification apparatus and the patient interface. The humidification apparatus may comprise a humidification chamber configured to hold a volume of liquid.

In another embodiment, the supply tube may define the gases flow path between the gases source and the humidification apparatus In a further embodiment, the filter assembly may be adjacent to or within the patient interface. The delivery tube may comprise the filter assembly at a patient interface end.

In one embodiment, the filter assembly may be adjacent to or within the humidification apparatus. The delivery tube may comprise the filter assembly at a gases source end.

In another embodiment, the at least one heating element may extend through the delivery tube.

In a further embodiment, the patient interface may comprise a trocar or a cannula for laparoscopic surgery.

In one embodiment, the patient interface may comprise a diffuser for use in open surgery.

In another embodiment, the gases source may comprise a carbon dioxide supply.

In an eight aspect, the invention consists of an insufflation system including: a gases source; a patient interface; a delivery conduit configured to defined a gases flow path between the gases source and the patient interface; and a filter assembly forming part of the gases flow path, the filter assembly comprising: a filter medium operative to filter humidified gases; a housing comprising an inlet, an outlet and the filter medium, the housing defining a gases flow path through the filter medium between the inlet and the outlet; and at least one heating element being positioned in the housing and being configured to heat the humidified gases flowing through the gases flow path; and wherein, the at least one heating element is positioned in the gases flow path downstream from the filter medium.

In one embodiment, the insufflation system may further comprise a humidification apparatus configured to be placed in the gases flow path between the gases source and the patient interface such that the delivery conduit defines the gases flow path between the humidification apparatus and the patient interface. The humidification apparatus may comprise a humidification chamber configured to hold a volume of liquid.

In another embodiment, the supply tube may define the gases flow path between the gases source and the humidification apparatus In a further embodiment, the filter assembly may be adjacent to or within the patient interface. The delivery tube may comprise the filter assembly at a patient interface end.

In one embodiment, the filter assembly may be adjacent to or within the humidification apparatus. The delivery tube may comprise the filter assembly at a gases source end.

In another embodiment, the at least one heating element may extend through the delivery tube.

In a further embodiment, the patient interface may comprise a trocar or a cannula for laparoscopic surgery.

In one embodiment, the patient interface may comprise a diffuser for use in open surgery.

In another embodiment, the gases source may comprise a carbon dioxide supply.

In a ninth aspect, the invention consists in an insufflation system including: a gases source; a patient interface; a delivery conduit configured to defined a gases flow path between the gases source and the patient interface; and an elbow filter forming part of the gases flow path, the elbow filter comprising: a filter medium operative to filter humidified gases; a housing comprising an inlet, an outlet and the filter medium, the housing defining a gases flow path through the filter medium between the inlet and the outlet; and wherein, said filter medium is positioned within the housing to span said inlet, and wherein the inlet and the outlet are oriented so that the housing form an elbow.

In one embodiment, the insufflation system may further comprise a humidification apparatus configured to be placed in the gases flow path between the gases source and the patient interface such that the delivery conduit defines the gases flow path between the humidification apparatus and the patient interface. The humidification apparatus may comprise a humidification chamber configured to hold a volume of liquid.

In another embodiment, the supply tube may define the gases flow path between the gases source and the humidification apparatus In a further embodiment, the elbow filter may be adjacent to or within the patient interface. The delivery tube may comprise the elbow filter at a patient interface end.

In one embodiment, the elbow filter may be adjacent to or within the humidification apparatus. The delivery tube may comprise the elbow filter at a gases source end.

In a further embodiment, the at least one heating element may extend through the delivery tube.

In one embodiment, the patient interface may comprise a trocar or a cannula for laparoscopic surgery.

In another embodiment, the patient interface may comprise a diffuser for use in open surgery.

In a further embodiment, the gases source may comprise a carbon dioxide supply.

In a tenth aspect, the invention consists in a respiratory system including: a gases source; a patient interface; a delivery conduit configured to defined a gases flow path between the gases source and the patient interface; and a filter assembly forming part of the gases flow path, the filter assembly comprising: a filter medium operative to filter medical gases; a housing comprising an inlet, an outlet and the filter medium, the housing defining a gases flow path through the filter medium between the inlet and the outlet; and at least one heating element being positioned in the housing and being configured to heat the filter medium; and wherein, the at least one heating element is spaced apart from the filter medium and an inner surface of the housing.

In one embodiment, the respiratory system may comprise a positive airway pressure apparatus, a high-flow apparatus, a wall source of gas, or a ventilator.

In another embodiment, the patient interface may comprise a nasal cannula, a full-face mask, a nasal mask, a nasal pillows interface, a tracheotomy interface, or an entrotracheal tube.

In an eleventh aspect, the invention consists of an insufflation system including: a gases source; a patient interface; a delivery conduit configured to defined a gases flow path between the gases source and the patient interface; and a filter assembly forming part of the gases flow path, the filter assembly comprising: a filter medium operative to filter humidified gases; a housing comprising an inlet, an outlet and the filter medium, the housing defining a gases flow path through the filter medium between the inlet and the outlet; and at least one heating element being positioned in the housing and being configured to heat the humidified gases flowing through the gases flow path; and wherein, the at least one heating element is positioned in the gases flow path downstream from the filter medium.

In one embodiment, the respiratory system may comprise a positive airway pressure apparatus, a high-flow apparatus, a wall source of gas, or a ventilator.

In another embodiment, the patient interface may comprise a nasal cannula, a full-face mask, a nasal mask, a nasal pillows interface, a tracheotomy interface, or an entrotracheal tube.

In a twelfth aspect, the invention consists in an insufflation system including: a gases source; a patient interface; a delivery conduit configured to defined a gases flow path between the gases source and the patient interface; and an elbow filter forming part of the gases flow path, the elbow filter comprising: a filter medium operative to filter humidified gases; a housing comprising an inlet, an outlet and the filter medium, the housing defining a gases flow path through the filter medium between the inlet and the outlet; and wherein, said filter medium is positioned within the housing to span said inlet, and wherein the inlet and the outlet are oriented so that the housing form an elbow.

In one embodiment, the respiratory system may comprise a positive airway pressure apparatus, a high-flow apparatus, a wall source of gas, or a ventilator.

In another embodiment, the patient interface may comprise a nasal cannula, a full-face mask, a nasal mask, a nasal pillows interface, a tracheotomy interface, or an entrotracheal tube.

In a thirtieth aspect, the invention consists in a filter assembly for use in an insufflation system, the filter assembly including: a filter medium operative to filter medical gases; a housing comprising an inlet, an outlet and the filter medium, the housing defining a gases flow path through the filter medium between the inlet and the outlet; and at least one heating element being positioned in the housing and being configured to heat the filter medium; wherein, the at least one heating element is spaced apart from the filter medium and from an inner surface of the housing.

In one embodiment, the at least one heating element may comprise one or more heater wires.

In another embodiment, the outlet of the housing may be operative to be coupled to a patient conduit, optionally the patient conduit may be configured to deliver the humidified gases passing through the filter assembly to the patient. The patient conduit may be permanently or removably attached to the outlet. The at least one heating element may be configured to extend along a length of the patient conduit. The patient conduit may comprise heating wires configured to heat gases flowing through the patient conduit.

In a further embodiment, the heating wires may be attached to or comprise the at least one heating element of the filter assembly.

In one embodiment, the filter assembly may further comprise an electrical power source coupling for supplying power to the at least one heating element.

In another embodiment, the filter assembly may be sterile.

In a further embodiment, the filter medium may comprise one or more of the following: a membrane; a glass-based material, a hydrophilic material; paper; and a pleated material; optionally, the filter medium may comprise parallel pleats.

In one embodiment, the filter assembly may further comprise at least one sensor positioned in the gases flow path between the inlet and the outlet of the housing; optionally, the sensor may be operative to measure data relevant to one or more of the following: a temperature; humidity; a pressure; and a flow rate of the gases flow.

In another embodiment, the inlet of the housing may be operative to be coupled to a humidification chamber.

In a further embodiment, the housing may comprise an electrical connector to provide for an electrical connection to the at least one heating element.

In one embodiment, the insufflation system may comprise a humidification apparatus operative to humidify the medical gases for delivery to a patient, and the filter assembly may be positioned in use between the humidification apparatus and the patient. The filter assembly may be positioned in use adjacent to a humidification chamber of the humidification apparatus.

In a further embodiment, the at least one heating element may be positioned in the gases flow path between the inlet and the outlet of the housing.

In a fourteenth aspect, the invention consists in a filter assembly for use in an insufflation system, the filter assembly comprising: a filter medium operative to filter humidified gases; a housing comprising an inlet, an outlet and the filter medium, the housing defining a gases flow path through the filter medium between the inlet and the outlet; and at least one heating element being positioned in the housing and being configured to heat the humidified gases flowing through the gases flow path; wherein, the at least one heating element is positioned in the gases flow path downstream from the filter medium.

In one embodiment, the at least one heating element may comprise one or more heater wires.

In another embodiment, the outlet of the housing may be operative to be coupled to a patient conduit, optionally the patient conduit may be configured to deliver the humidified gases passing through the filter assembly to the patient. The patient conduit may be permanently or removably attached to the outlet. The at least one heating element may be configured to extend along a length of the patient conduit. The patient conduit may comprise heating wires configured to heat gases flowing through the patient conduit.

In a further embodiment, the heating wires may be attached to or comprise the at least one heating element of the filter assembly.

In one embodiment, the filter assembly may further comprise an electrical power source coupling for supplying power to the at least one heating element.

In another embodiment, the filter assembly may be sterile.

In a further embodiment, the filter medium may comprise one or more of the following: a membrane; a glass-based material, a hydrophilic material; paper; and a pleated material; optionally, the filter medium may comprise parallel pleats.

In one embodiment, the filter assembly may further comprise at least one sensor positioned in the gases flow path between the inlet and the outlet of the housing; optionally, the sensor may be operative to measure data relevant to one or more of the following: a temperature; humidity; a pressure; and a flow rate of the gases flow.

In another embodiment, the inlet of the housing may be operative to be coupled to a humidification chamber.

In a further embodiment, the housing may comprise an electrical connector to provide for an electrical connection to the at least one heating element.

In one embodiment, the insufflation system may comprise a humidification apparatus operative to humidify the medical gases for delivery to a patient, and the filter assembly may be positioned in use between the humidification apparatus and the patient. The filter assembly may be positioned in use adjacent to a humidification chamber of the humidification apparatus.

In a further embodiment, the at least one heating element may be positioned in the gases flow path between the inlet and the outlet of the housing.

In a fifteenth aspect, the invention consists in an insufflation system including: a filter assembly including: a filter medium operative to filter humidified gases; a housing comprising an inlet, an outlet and the filter medium, the housing defining a gases flow path through the filter medium between the inlet and the outlet; and at least one heating element configured to heat the humidified gases flowing through the gases flow path; and, a patient conduit connected to the outlet of the housing, wherein the at least one heating element extends along at least part of a length of the patient conduit.

In one embodiment, the at least one heating element may comprise one or more heater wires.

In another embodiment, the outlet of the housing may be operative to be coupled to a patient conduit, optionally the patient conduit may be configured to deliver the humidified gases passing through the filter assembly to the patient. The patient conduit may be permanently or removably attached to the outlet. The at least one heating element may be configured to extend along a substantial portion of a length of the patient conduit. The patient conduit may comprise heating wires configured to heat gases flowing through the patient conduit.

In a further embodiment, the heating wires may be attached to or comprise the at least one heating element of the filter assembly.

In one embodiment, the filter assembly may further comprise an electrical power source coupling for supplying power to the at least one heating element.

In another embodiment, the filter assembly may be sterile.

In a further embodiment, the filter medium may comprise one or more of the following: a membrane; a glass-based material, a hydrophilic material; paper; and a pleated material; optionally, the filter medium may comprise parallel pleats.

In one embodiment, the filter assembly may further comprise at least one sensor positioned in the gases flow path between the inlet and the outlet of the housing; optionally, the sensor may be operative to measure data relevant to one or more of the following: a temperature; humidity; a pressure; and a flow rate of the gases flow.

In another embodiment, the inlet of the housing may be operative to be coupled to a humidification chamber.

In a further embodiment, the housing may comprise an electrical connector to provide for an electrical connection to the at least one heating element.

In one embodiment, the insufflation system may comprise a humidification apparatus operative to humidify the medical gases for delivery to a patient, and the filter assembly may be positioned in use between the humidification apparatus and the patient. The filter assembly may be positioned in use adjacent to a humidification chamber of the humidification apparatus.

In a further embodiment, the at least one heating element may be positioned in the gases flow path between the inlet and the outlet of the housing.

In one embodiment, the at least one heating element may be positioned in the gases flow path downstream from the filter medium. The at least one heating element may be positioned in the housing. The at least one heating element may be positioned around, or proximate to, the housing.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

One preferred form of the present invention will now be described with reference to the accompanying drawings in which:

FIG. 6A is an isometric view of the filter assembly of FIG. 2, constructed and operative in accordance with an embodiment of the invention;

FIG. 6B is a cross sectional view of the filter assembly of FIG. 6A;

DETAILED DESCRIPTION

In the following description, numerous specific details are set forth in order to provide a thorough understanding of the various principles of the present invention. However, those skilled in the art will appreciate that not all these details are necessarily always required for practicing the present invention.

Although the principles of the present invention are largely described herein in relation to laparoscopy or open surgery procedures, this is an example selected for convenience of presentation, and is not limiting. The filter assemblies described herein may be used for any suitable medical procedure and in any suitable medical system comprising a gas delivery circuit, such as a gas delivery system for delivering respiratory gases.

Figure 1:
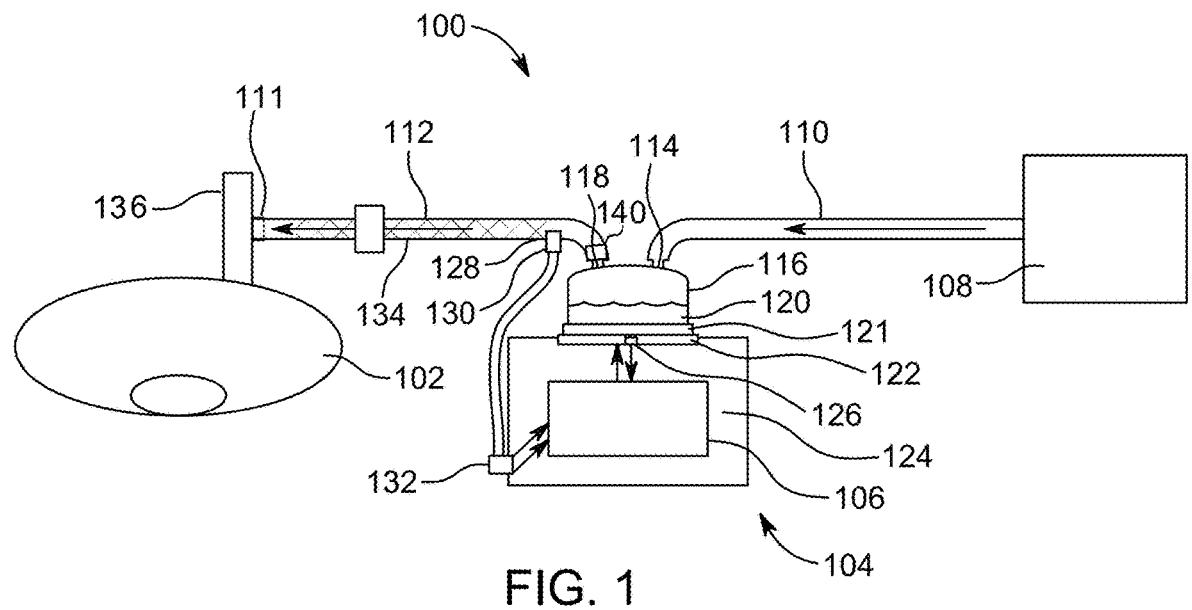
FIG. 1 is a schematic view of an insufflation system comprising a filter assembly, constructed and operative in accordance with an embodiment of the invention.

Reference is now made to FIG. 1, which is a schematic view of an insufflation system comprising a filter assembly constructed and operative in accordance with an embodiment of the present invention.

FIG. 1 illustrates an insufflation system 100 for delivering temperature- and humidity-controlled gas to a patient 102, the insufflation system 100 having a humidification apparatus or humidifier 104 incorporating a humidifier control system 106. The humidifier 104 is connected to a gas source 108 through an inlet conduit 110. The humidifier 104 delivers humidified gas to the patient 102 through a patient conduit 112. The conduits 110, 112 may be made of flexible plastic tubing.

The humidifier 104 receives, at an inlet 114, gas from the gas source 108 through the inlet conduit 110. The gas is humidified as it passes through a humidifying chamber 116, which is effectively a water bath, or passover humidifier, and the gas flows out through a humidifier outlet 118 and into the patient conduit 112. The gas may be filtered through a filter assembly 140 and delivered to the patient 102 through the patient conduit 112, Luer connector 111 and the patient interface 136. The patient interface 136 may be, for example, but not limited to, a trocar or cannula for laparoscopic surgery or a diffuser for open surgery. According to an embodiment, the system may be for delivering respiratory gases rather than insufflation gases, and in this embodiment the patient interface may be, for example, a nasal cannula, full-face mask, nasal mask, nasal pillows interface, tracheostomy interface or endotracheal tube.

The humidifier 104 comprises a body 124 removably engageable with the humidification chamber 116. The humidification chamber 116 has a metal base 121 and is adapted to hold a volume of water 120, which can be heated by a heater plate 122. The heater plate 122 may be in thermal contact with the metal base 121 of the humidification chamber 116. Providing power to the heater plate 122 may cause heat to flow from the heater plate 122 to the water 120 through the metal base 121. As the water 120 within the humidification chamber 116 is heated it may evaporate and the evaporated water can mix with gases flowing through the humidification chamber 116 from the gas source 108. Accordingly, the humidified gases leave the humidification chamber 116 via outlet 118 and are passed to the patient 102 via the patient conduit 112, the filter assembly 140, the Luer connector 111, the patient interface 136 and into the surgical site to, for example, insufflate the surgical site and/or expand body cavity.

The humidifier 104 includes the humidifier control system 106 configured to control a temperature and/or humidity of the gas being delivered to the patient 102. The humidifier control system 106 may be configured to regulate an amount of humidity supplied to the gases by controlling an electrical power supplied to the heater base 122. The humidifier control system 106 may control operation of the humidification system 104 in accordance with instructions set in software and in response to system inputs. System inputs may include a heater plate sensor 126, an outlet chamber temperature sensor 128, and a chamber outlet flow sensor 130. For example, the humidifier control system 106 may receive temperature information from the heater plate sensor 126 which it may use as an input to a control module used to control the power or temperature set point of the heater plate 122. The humidifier control system 106 may be provided with inputs of temperature and/or flow rates of the gases. For example, the chamber outlet temperature sensor 128 may be provided to indicate to the humidifier control system 106 the temperature of the humidified gas as it leaves the outlet 118 of the humidification chamber 116. The temperature of the gases exiting the chamber may be measured using any suitable temperature sensor 128, such as a wire-based temperature sensor. The chamber outlet flow sensor 130 may be provided to indicate to the humidifier control system 106 the flow rate of the humidified gas. The flow rate of the gases through the chamber 116 may be measured using any suitable flow sensor 130, such as a hot wire anemometer. In some embodiments, the temperature sensor 128 and flow sensor 130 are in the same sensor housing. The temperature sensor 128 and flow sensor 130 may be connected to the humidifier 104 via connector 132. Additional sensors may be incorporated into the insufflation system 100, for example, for sensing parameters at the patient end of the patient conduit 112.

The humidifier control system 106 may be in communication with the heater plate 122 such that the humidifier control system 106 may control a power delivered to the heater plate 122 and/or control a temperature set point of the heater plate 122. The humidifier control system 106 may determine an amount of power to deliver to the heater plate 122, or a heater plate set point, based at least in part on a flow condition, an operation mode, a flow reading, an outlet temperature reading, a heater plate sensor reading, or any combination of these or other factors.

The insufflation system 100 may include a conduit heating wire 134 configured to provide heat to the gases traveling along the patient conduit 112. Gases leaving the outlet 118 of the humidification chamber 116 may have a high relative humidity (e.g., about 100%). As the gases travel along the patient conduit 112 there is a chance that water vapor may condense on the conduit wall, reducing the water content of the gases. To reduce condensation of the gases within the conduit, the conduit heating wire 134 may be provided within, throughout, and/or around the patient conduit 112. Power may be supplied to the conduit heating wire 134 from the humidifier 104 and may be controlled through the humidifier control system 106. In some embodiments, the heating wire 134 is configured to maintain the temperature of the gas flowing through the patient conduit 112. In some embodiments, the conduit heating wire 134 may be configured to provide additional heating of the gas to elevate the gases temperature to maintain the humidity generated by the heated water bath in the humidifier 104.

The filter assembly 140 may be configured to filter the humidified gases exiting the humidification chamber 116 so as to deliver filtered humidified gases to the patient 102 through the patient conduit 112, the Luer connector 111 and the patient interface 136. In FIG. 1, the filter assembly 140 is shown as being positioned in a median zone of the patient conduit 112 between the Luer connector 111/patient interface 136 and the humidifier 104. Those skilled in the art will however appreciate that this configuration is provided as an example only and is not limiting. The filter assembly 140 may be positioned at any suitable position in the wet-side of the insufflation system 100 i.e. between the humidifier 104 and the patient interface 136. For example, but not limited to, the filter assembly 140 may be positioned adjacent to the humidifier 104, in the humidification chamber 116, adjacent to and/or in the Luer connector 111/patient interface 136.

The filter assembly 140 may comprise a housing, a filter medium and heating means. The housing may comprise an inlet and an outlet and be configured to receive the filter medium. The humidified gases may therefore enter the filter assembly by the housing inlet, pass through the filter medium and exit the filter assembly by the housing outlet. Non-limiting examples of filter medium includes a membrane, a glass-based or hydrophobic material, paper, pleated material (e.g. preferably linear parallel pleats), etc. The heating means may be any suitable means adapted to heat actively or passively the filter assembly 140 so as to prevent condensation clogging the filter medium. Active heating means may include, for example, but not limited to, a heated mesh on the filter medium, a heated conductive plastic housing, heater wires (e.g. in the gases flow path defined by the housing but spaced apart from the housing or attached and/or embedded in the housing), heating elements electrically or thermally coupled to the humidifier 104, etc. Passive heating means may include, for example, but not limited to, designing the insufflation system 100 and the filter assembly 140 so that the heated gases flow is redirected and used to heat the filter assembly 140 before or after passing through the filter medium, using heat loss from the humidification chamber 116 to heat the filter assembly 140, etc.

Figure 2:
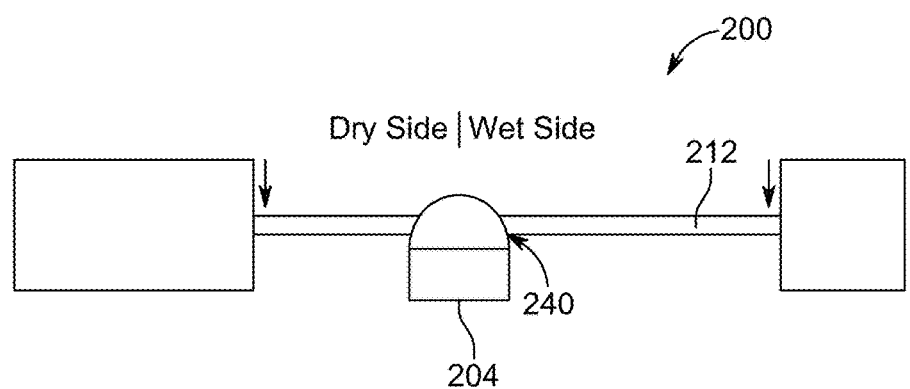
FIG. 2 is a schematic view of an insufflation system comprising a filter assembly adjacent to a humidification apparatus, constructed and operative in accordance with another embodiment of the invention.

Reference is now made to FIG. 2, which is a schematic view of a filter assembly, constructed and operative in accordance with an embodiment of the present invention.

FIG. 2 illustrates a filter assembly 240 positioned in use adjacent to the humidifier 204 of the insufflation system 200 between the humidification chamber and the patient conduit 212. The filter assembly 240 may, for instance, be provided as part of a connector (e.g. elbow connector) configured to connect the outlet of the humidification chamber to the patient conduit 212. This connector may be integral with the patient conduit 212 or provided as a component separate from the patient conduit 212. In another example, the filter assembly 240 may be provided as a separate unit operative to be removably coupled to the humidification chamber. The filter assembly 240 may comprise a connecting portion arranged to be coupled to the cylindrical wall of the humidification chamber outlet. In a further example, the filter assembly 240 may be permanently coupled to the humidification chamber outlet by welding, overmoulding, using a snap-fit connection, etc. Further embodiments of the present invention comprising a filter assembly adjacent to the humidifier 240 will be described in relation to FIGS. 3A to 7B.

The filter assembly 240 may also comprise heating means configured to reduce condensation on the filter medium and the filter housing. The heating means may be any suitable heating elements operative to maintain the gas temperature above the dew point temperature. The heat may be applied by the heating elements directly to the filter medium or to the filter housing as it will apparent hereinafter.

Figure 3A:
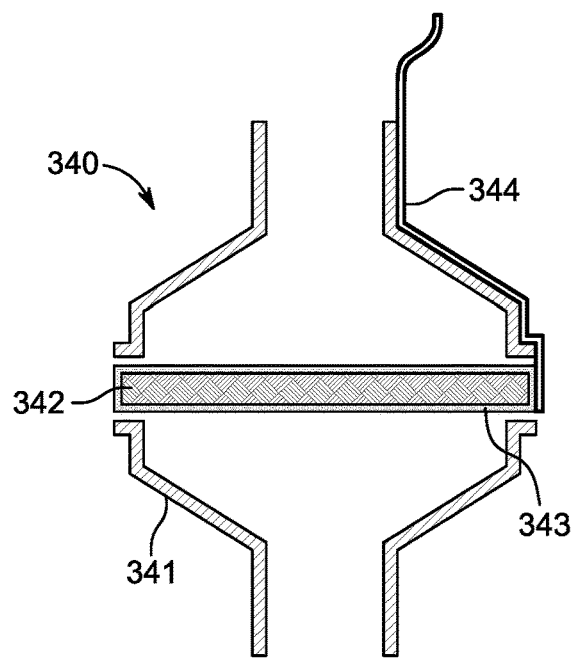
FIG. 3A is a cross sectional view of the filter assembly of FIG. 2, constructed and operative in accordance with an embodiment of the invention.
Figure 3B:
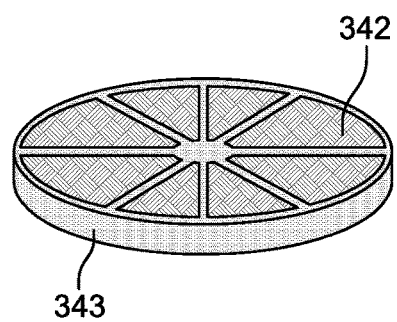
FIGS. 3B and 3C are isometric views of the filter assembly of FIG. 3A.
Figure 3C:
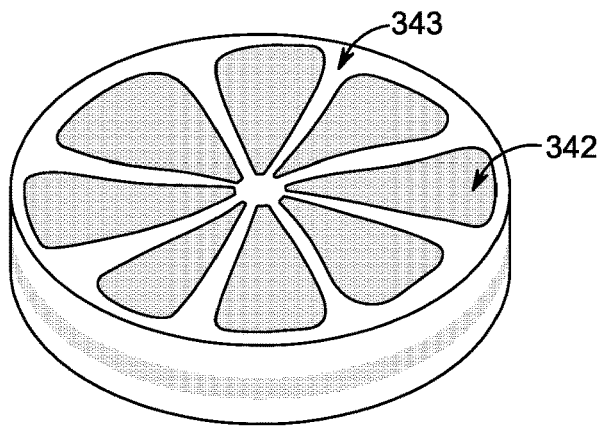

Reference is now made to FIGS. 3A to 3C, which are views of the filter assembly of FIG. 2, constructed and operative in accordance with an embodiment of the present invention.

FIG. 3A shows a filter assembly 340 comprising a housing 341, a filter medium 342 and heating elements 343, 344. The housing 341 comprises an inlet operative to be coupled to an outlet of the humidification chamber and an outlet operative to be coupled to the patient conduit. The housing 341 further comprises a filter medium 342 disposed in use between the inlet and the outlet of the housing 341 so that humidified gases entering the housing 341 at the inlet pass through the filter medium 342 before exiting the housing 341 at the outlet. The filter assembly 340 also comprises a heating element 343 operative to be connected to a power supply. For example, the heating element 343 may be a thermoconductive plastic that may be heated by electrical wires connected to the power source of the humidifier heater base or any other suitable power source. As it is apparent from FIGS. 3B and 3C, the heating element 343 may comprise holes filled with the filter medium 342. When the heating element 343 is heated, the filled medium 342 is therefore heated so as to reduce condensation in the filter assembly 340.

Figure 4A:
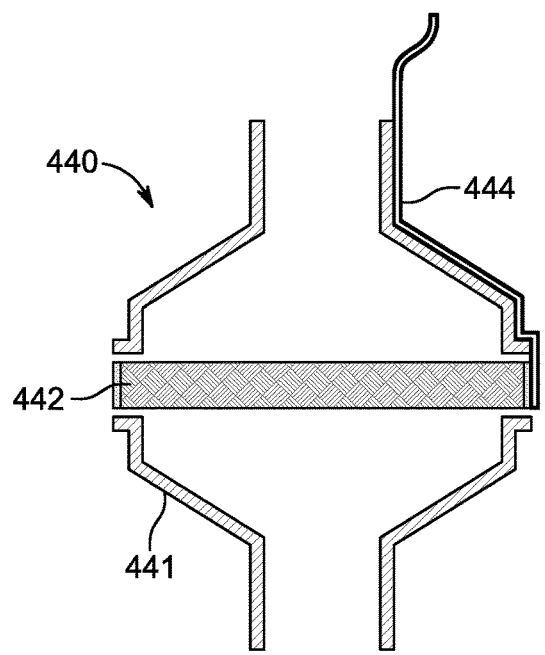
FIG. 4A is a cross sectional view of the filter assembly of FIG. 2, constructed and operative in accordance with another embodiment of the invention.
Figure 4B:
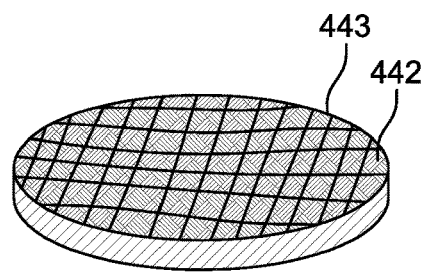
FIG. 4B is an isometric view of the filter assembly of FIG. 4A.

Reference is now made to FIGS. 4A and 4B, which are views of the filter assembly of FIG. 2, constructed and operative in accordance with another embodiment of the present invention.

FIG. 4A illustrates a filter assembly 440 similar to the filter assembly 340 of FIG. 3A. The filter assembly 440 also comprises a housing 441, a filter medium 442 and heating elements 443, 444. In this exemplary embodiment of the present invention, however, the heating element 443 connected to the power supply is provided as a resistive wire mesh insert disposed in use on an external surface of the filter medium 442. When the heating element 443 is heated, the filter medium 442 is therefore heated so as to reduce condensation in the filter assembly 440.

Figure 5:
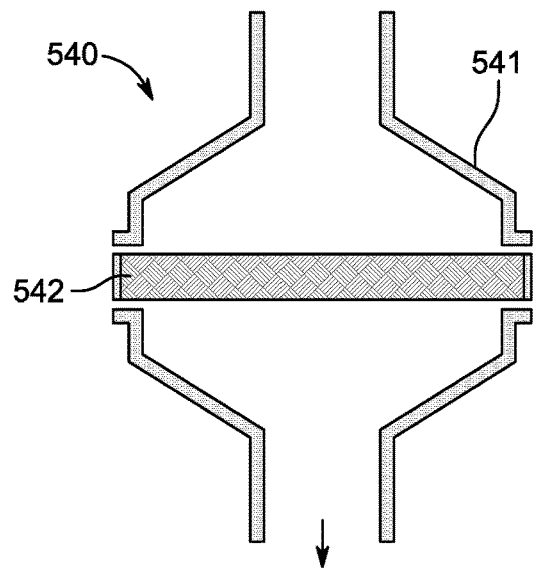
FIG. 5 is a cross sectional view of the filter assembly of FIG. 2, constructed and operative in accordance with a further embodiment of the invention.

Reference is now made to FIG. 5, which is a cross sectional view of the filter assembly of FIG. 2, constructed and operative in accordance with a further embodiment of the present invention.

FIG. 5 illustrates a filter assembly 540 similar to the filter assemblies 340 and 440 described hereinabove. The filter assembly 540, however, does not comprise a separate heating element. The housing 541 is preferably made of a thermoconductive plastic material that can be heated by any suitable power source. Therefore, the housing 541 is and/or acts as a heating element so as to heat the filter medium 542 and reduce condensation in the filter assembly 540.

Reference is now made to FIGS. 6A and 6B, which are views of the filter assembly of FIG. 2, constructed and operative in accordance with an embodiment of the present invention.

FIG. 6A shows a filter assembly 640 positioned in use adjacent to the humidifier between the outlet of the humidification chamber 616 and the patient conduit 612. The filter assembly 640 comprises a housing 641, a filter medium 642 and heating elements 643, 644. The housing 641 comprises an inlet operative to be coupled to an outlet of the humidification chamber and an outlet operative to be coupled to the patient conduit 612. The housing 641 further comprises a filter medium 642 disposed in use between the inlet and the outlet of the housing 641 so that humidified gases entering the housing 641 at the inlet pass through the filter medium 642 before exiting the housing 641 at the outlet.

FIG. 6B is a cross sectional view of the filter assembly 640 and shows the heating elements 643 positioned in an upper region of the housing 641 but spaced apart from the inner top surface. The heating elements 643 are preferably the heater wires of the patient conduit 612 extending through the housing 641 so as to be connected to the power supply. When the heating elements 643 are heated, the filter medium 642 is therefore heated so as to reduce condensation in the filter assembly 640.

Figures 7A, 7B:
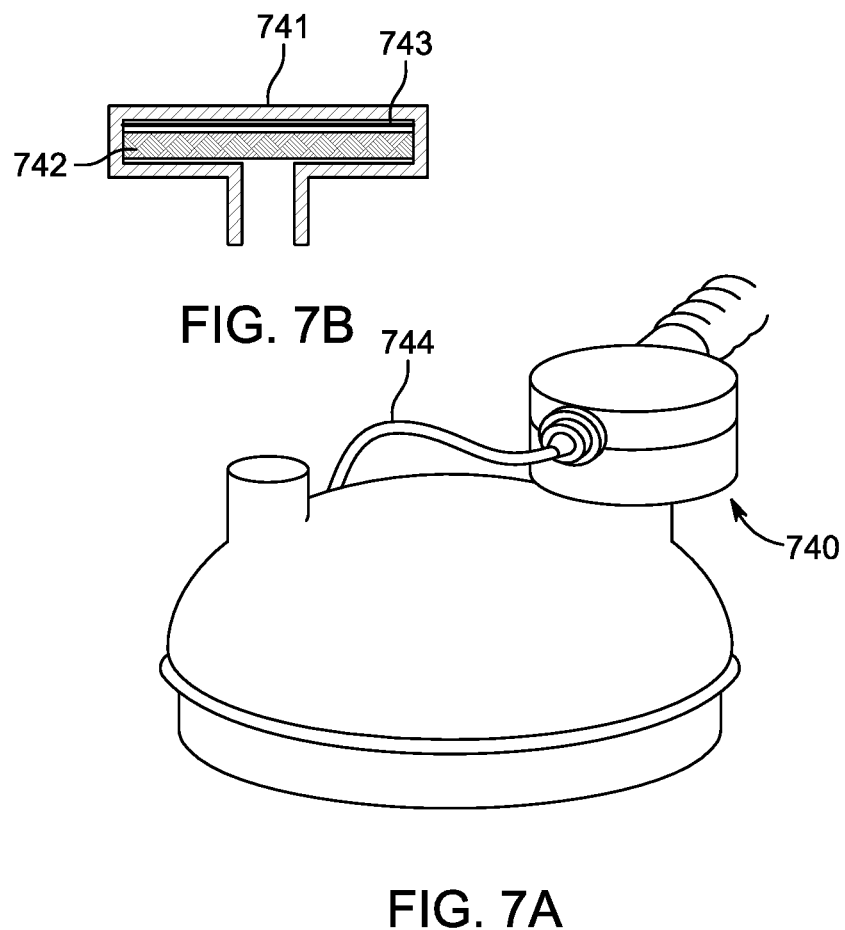
FIG. 7A is an isometric view of the filter assembly of FIG. 2, constructed and operative in accordance with another embodiment of the invention.
FIG. 7B is a cross sectional view of the filter assembly of FIG. 7A.

Reference is now made to FIGS. 7A and 7B, which are views of the filter assembly of FIG. 2, constructed and operative in accordance with another embodiment of the present invention.

FIGS. 7A and 7B illustrate a filter assembly 740 similar to the filter assembly 640 of FIGS. 6A and 6B. The filter assembly 740 also comprises a housing 741, a filter medium 742 and a heating element 743. In this exemplary embodiment, however, the heating element 743, connected to the power supply 744, is provided as a printed circuit board heater overmoulded into a top surface of the housing 741. When the heating element 743 is heated, the filter medium 742 is therefore heated so as to reduce condensation in the filter assembly 740.

Figure 8:
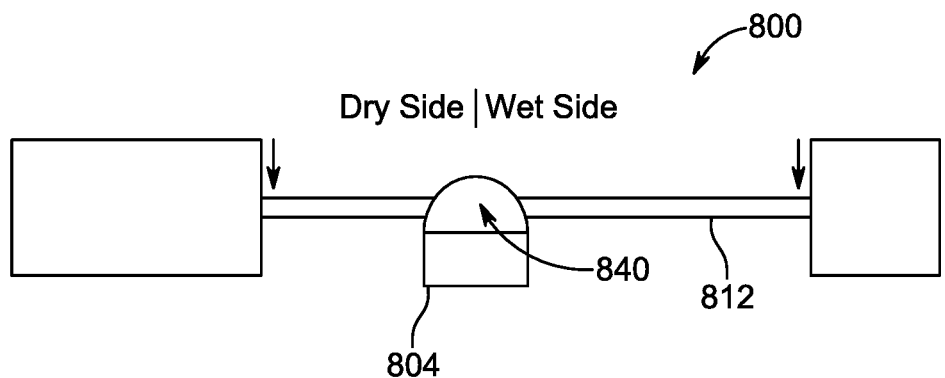
FIG. 8 is a schematic view of an insufflation system comprising a filter assembly embodied in a humidification apparatus, constructed and operative in accordance with a further embodiment of the invention.

Reference is now made to FIG. 8, which is a schematic view of a filter assembly, constructed and operative in accordance with another embodiment of the present invention.

FIG. 8 illustrates a filter assembly 840 positioned in use within the humidifier 804 of the insufflation system 800 between the inlet and the outlet of the humidification chamber. The filter assembly 840 may, for instance, be provided as part of a medical taper that is configured to connect the outlet of the humidification chamber to the patient conduit 812. In another example, the filter assembly 840 may be positioned within the humidification chamber. Further embodiments of the present invention comprising a filter assembly within the humidifier chamber will be described in relation to FIGS. 9 to 11.

The filter assembly 840 of FIG. 8 may also comprise heating means configured to reduce condensation on the filter medium and the filter housing. The heating means may be any suitable heating elements operative to maintain the filter medium at a particular temperature (i.e. gas temperature being greater than the dew temperature) due to its location within the humidification chamber.

Figure 9A:
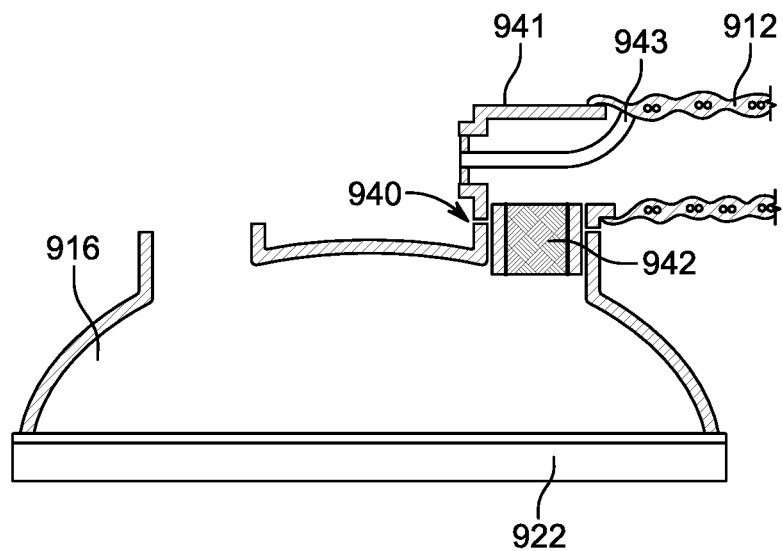
FIGS. 9A and 9B are cross sectional views of the filter assembly of FIG. 8, constructed and operative in accordance with embodiments of the invention.
Figure 9B:
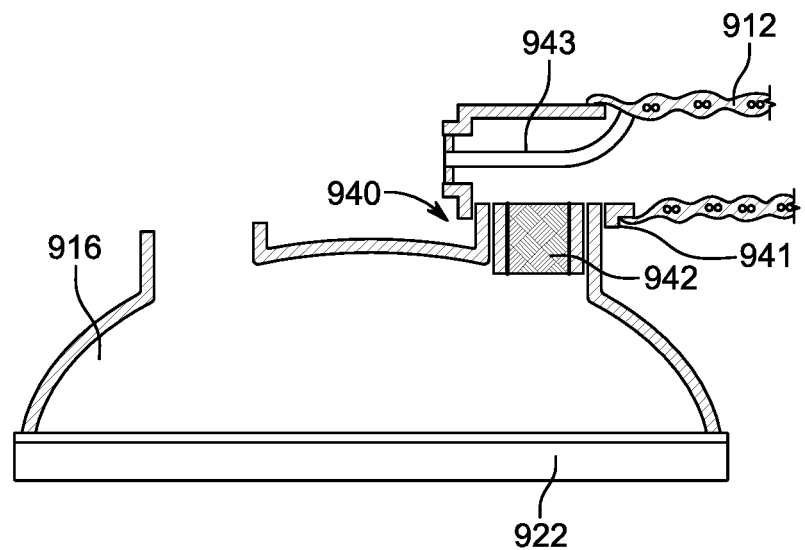

Reference is now made to FIGS. 9A and 9B, which are cross sectional views of the filter assembly of FIG. 8, constructed and operative in accordance with embodiments of the present invention.

FIG. 9A shows a filter assembly 940 comprising a housing 941, a filter medium 942 and heating elements 943. The housing 941 may be made of a plastic material and may correspond to a portion of a medical taper configured to push-fit into the outlet of the humidification chamber 916 to connect the humidification chamber 916 to the patient conduit 912. FIG. 9A also shows the filter medium 942 being provided as a push-fit insert that protrudes from the outlet of the humidification chamber 916, such that the housing 941 attaches to the humidification chamber 916 by friction fit with the filter medium 942. In use, humidified gases entering at an inlet of the housing 941 pass through the filter medium 942 before exiting the housing 941 at an outlet. The filter medium 942 may be heated by the heating element 943 corresponding to the heater wires of the patient conduit 912 and extending through an upper region of, but spaced apart from, the housing 941. Additionally and/or alternatively, the heating element 943 may comprise the heater plate 922 of the humidifier which may be configured to heat the water present in the humidification chamber 916. The heat may pervade the humidification chamber 916 to heat and/or maintain the filter medium 942 at a particular temperature so that condensation may be reduced in the filter assembly 940.

FIG. 9B shows a filter assembly 940 similar to the one described in relation to FIG. 9A. The filter medium 942 is however provided as a push-fit insert that is fully inserted into the outlet of the humidification chamber 916. In such embodiment of the present invention, the housing 941 may be connected to the outlet of the humidification chamber 916 by friction fit.

Figure 10A:
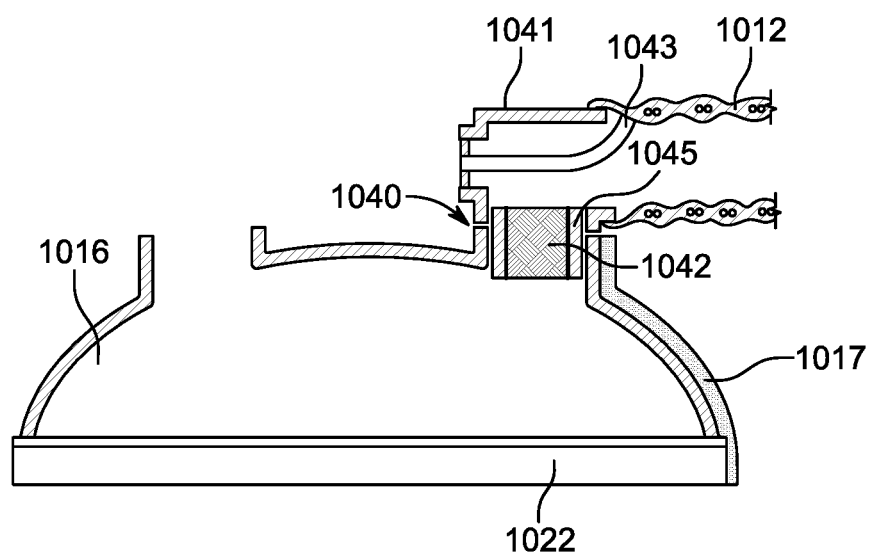
FIGS. 10A and 10B are cross sectional views of the filter assembly of FIG. 8, constructed and operative in accordance with other embodiments of the invention.
Figure 10B:
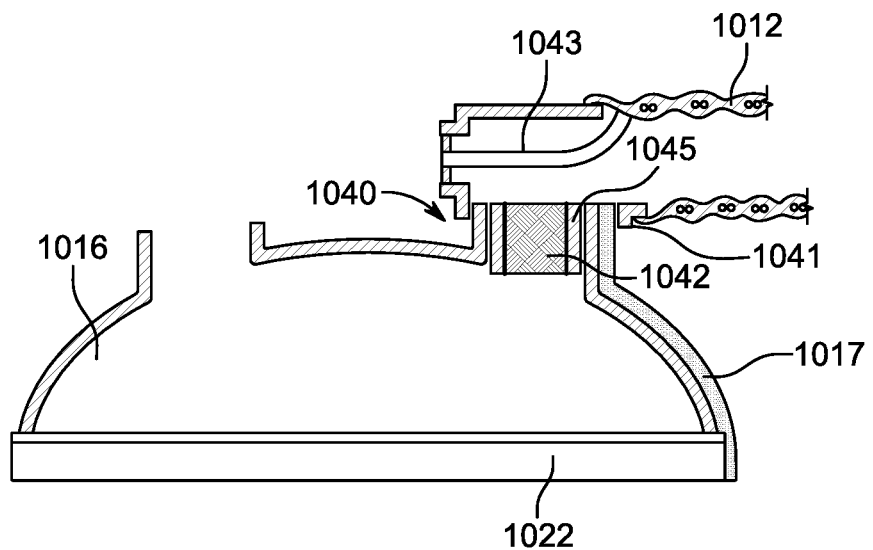

Reference is now made to FIGS. 10A and 10B, which are cross sectional views of the filter assembly of FIG. 8, constructed and operative in accordance of other embodiments of the present invention.

FIG. 10A shows a filter assembly 1040 similar to the filter assembly 940 of FIG. 9A. The filter assembly 1040 also comprises a housing 1041, a filter medium 1042 and a heating element 1043. In this exemplary embodiment, however, the humidification chamber 1016 may be at least partially overmoulded with a thermoconductive plastic element 1017. In addition, a thermoconductive plastic element 1045 may also be provided around the filter medium 1042. The filter medium 1042 may be heated by the heating element 1043 corresponding to the heater wires of the patient conduit 1012 and extending through an upper region of, but spaced apart from, the housing 1041. Additionally and/or alternatively, the heating element of the filter assembly 1040 may comprise the heater plate 1022, the thermoconductive plastic element 1017 of the humidification chamber 1016, and the thermoconductive plastic element 1045 surrounding the filter medium 1042. When the heater plate 1022 heats the water present in the humidification chamber 1016, the heat is conducted to the housing 1041 via the thermoconductive plastic elements 1017 and 1045 to heat the filter medium 1042 so as to reduce condensation in the filter assembly 1040.

FIG. 10B shows a filter assembly similar to the ones shown in FIGS. 9B and 10A. In such exemplary embodiment, the filter medium 1042 and its surrounding thermoconductive plastic element 1045 is provided as a push-fit insert that is fully inserted into the outlet of the humidification chamber 1016.

Figure 11:
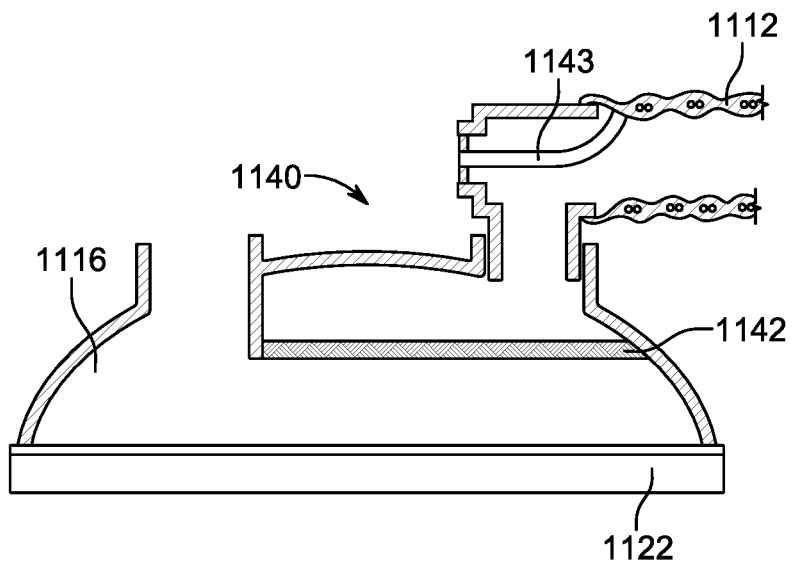
FIG. 11 is a cross sectional view of the filter assembly of FIG. 8, constructed and operative in accordance with a further embodiment of the invention.

Reference is now made to FIG. 11, which is a cross sectional view of the filter assembly of FIG. 8, constructed and operative in accordance with a further embodiment of the present invention.

FIG. 11 shows a humidification chamber 1116 connected to a patient conduit 1112 via a medical taper that push-fits into the humidification chamber outlet. The interior of the humidification chamber 1116 may be configured so as to permit a filter medium 1142 to be disposed in the flow path of humidified gases exiting the chamber. In such embodiment, the housing of the filter assembly 1140 may comprise a portion of the humidification chamber 1116. In addition, the heater plate 1122 of the humidifier may serve as the heating element of the filter assembly 1140 so as to heat the filter medium 1132 and reduce condensation in the filter assembly 1140.

Figure 12:
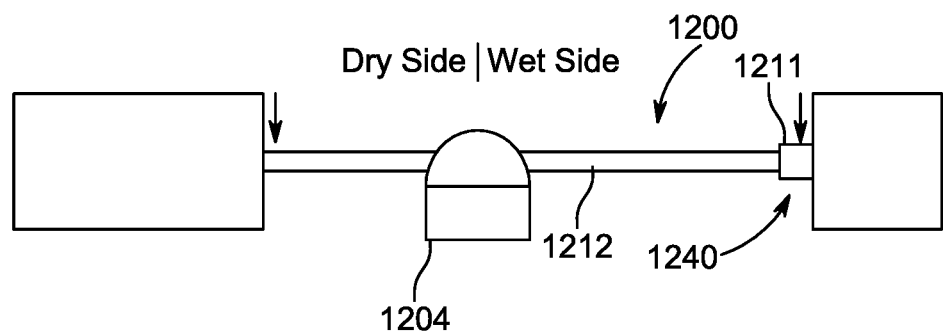
FIG. 12 is a schematic view of an insufflation system comprising a filter assembly positioned at a patient interface, constructed and operative in accordance with an embodiment of the invention.

Reference is now made to FIG. 12, which is a schematic view of a filter assembly, constructed and operative in accordance with an embodiment of the present invention.

FIG. 12 illustrates a filter assembly 1240 positioned in use adjacent to the patient interface 1236 of the insufflation system 1200. The filter assembly 1240 may, for instance, be provided as part of the Luer connector 1211 configured to connect the patient conduit 1212 to the patient interface 1236. Alternatively, the filter assembly 1240 may be provided as a standalone unit positioned in use between the patient conduit 1212 or the Luer connector 1211 and the patient interface 1236. In another example, the filter assembly 1240 may be integral with the patient interface 1236 and disposed in use inside the housing of the patient interface 1236. Further exemplary embodiments of the present invention comprising a filter assembly adjacent to the patient interface 1236 will be described in relation to FIGS. 13 to 18.

The filter assembly 1240 of FIG. 12 may comprise a housing, a filter medium and heating means. The heating means may be configured to reduce condensation on the filter medium and the filter housing. The heating means may be any suitable heating elements operative to maintain the gas temperature above the dew point temperature.

Figure 13:
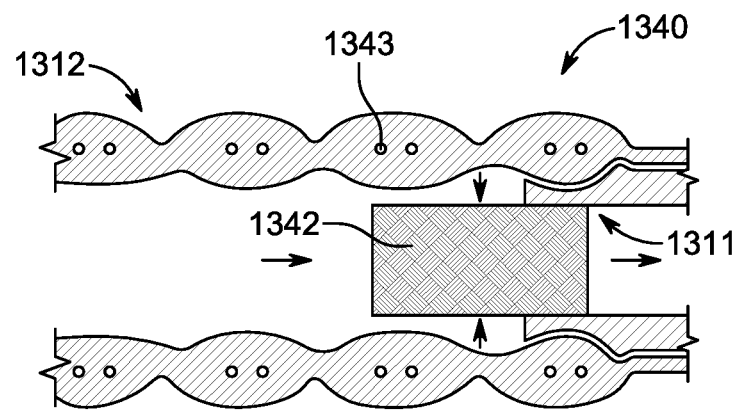
FIG. 13 is a cross sectional view of the filter assembly of FIG. 12, constructed and operative in accordance with another embodiment of the invention.

Reference is now made to FIG. 13, which is a cross sectional view of the filter assembly of FIG. 12, constructed and operative in accordance with an embodiment of the present invention.

FIG. 13 shows a patient conduit 1312 and a Luer connector 1311. The Luer connector 1311 is typically configured to connect the patient conduit 1312 to a patient interface (not shown). The tubing end of the Luer connector 1311 (i.e. the Luer connector end connecting to the patient conduit 1312) may be an insert made of a plastic material. This plastic insert may be configured to receive the filter medium 1342 so as to act as the housing of the filter assembly 1340. For example, the filter medium 1342 may be overmoulded onto or glued to the plastic insert. It will be apparent to those skilled in the art that the filter medium 1342 may be coupled to the Luer connector 1311 by any suitable means as long as humidified gases flowing though the patient conduit 1312 pass through the filter medium 1342 of the filter assembly 1340 before being delivered to the patient interface.

The patient conduit 1312 may comprise heating elements such as, for example, but not limited to, heating wires 1343. The heating wires 1343 incorporated into the tubing of the patient conduit 1312 may therefore heat the filter medium 1342 so that the gases are conditioned in a state that prevents condensation across the filter assembly 1340. The gases leaving the patient conduit 1312 may be heated at a temperature higher than a dew point temperature so as to compensate for heat losses associated with the parts of the filter assembly 1340/Luer connector 1311 and patient interface that are not heated. By heating the gases in the patient conduit 1312 to a temperature higher than the dew point, or to a temperature higher than the temperature desired at the patient, the gases have a relative humidity of less than 100% as they enter the filter assembly 1340 and are higher in temperature than is desired at the patient. The gases will then cool as they pass through the parts of the filter assembly 1340/Luer connector 1311 and patient interface that are not heated, and will be delivered to the patient at optimal humidity and/or temperature.

In another exemplary embodiment of the present invention, the insert of the Luer connector 1311 may be made of a thermoconductive plastic material and the heating wires of the patient conduit 1312 may be soldered to the insert. In such embodiment, the heat provided by the heating wires 1343 is conducted to the thermoconductive plastic insert which, in turn, heats directly the filter medium 1342 to reduce condensation in the filter assembly 1340.

Figure 14:
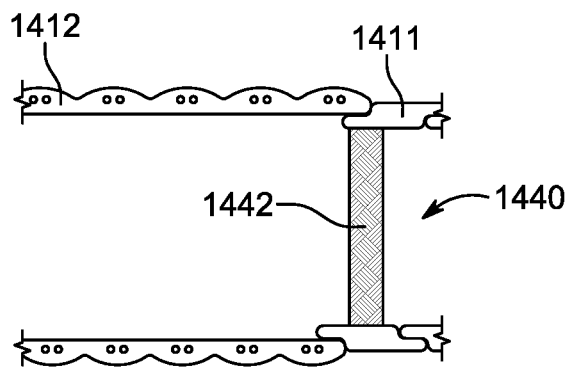
FIG. 14 is a cross sectional view of the filter assembly of FIG. 12, constructed and operative in accordance with a further embodiment of the invention.
Figure 15:
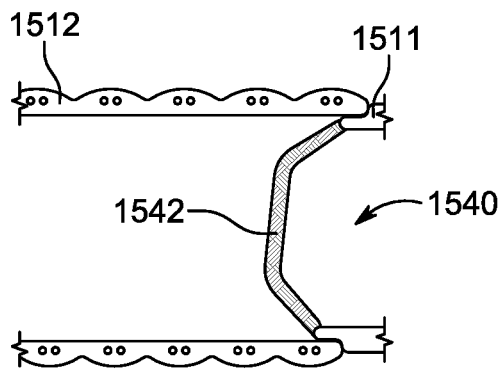
FIG. 15 is a cross sectional view of the filter assembly of FIG. 12, constructed and operative in accordance with an embodiment of the invention.
Figure 16:
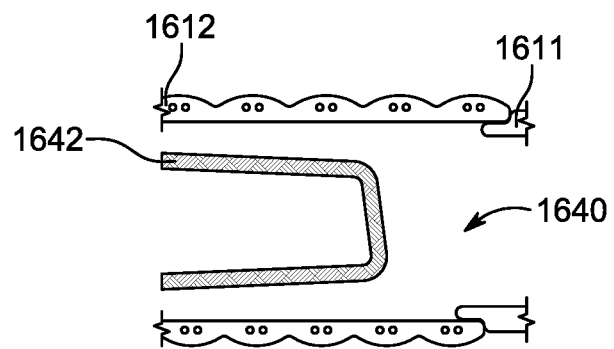
FIG. 16 is a cross sectional view of the filter assembly of FIG. 12, constructed and operative in accordance with another embodiment of the invention.

Reference is now made to FIGS. 14, 15 and 16, which are cross sectional views of the filter assembly of FIG. 12, constructed and operative in accordance with other embodiments of the present invention.

FIGS. 14 and 15 show different filter assemblies 1440 and 1540 similar to the one depicted in FIG. 13. In the exemplary embodiment of FIG. 14 however, the filter medium 1442 does not protrude from the Luer connector 1411. In the exemplary embodiment of FIG. 15, the filter medium 1542 may be provided as part of the Luer connector 1511 and lies partially within the patient conduit 1512.

FIG. 16 illustrates a filter assembly 1640 in which the filter medium 1642 is attached at the humidifier end of the patient conduit 1612 and lies within the patient conduit 1612. With such configuration, the gases flowing from the humidifier enter the filter medium 1642 and only pass through the lumen of the patient conduit 1612 by passing through the filter medium 1642.

Figure 17A:
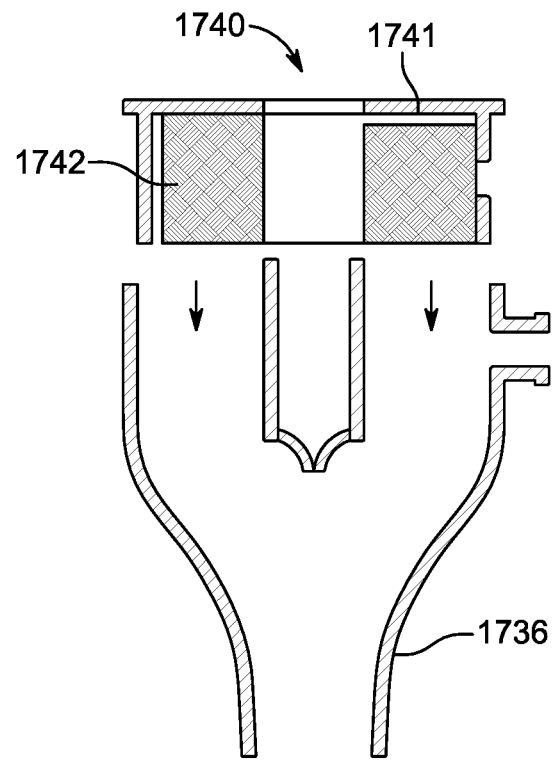
FIGS. 17A and 17B are cross sectional views of the filter assembly of FIG. 12, constructed and operative with a further embodiment of the invention.
Figure 17B:
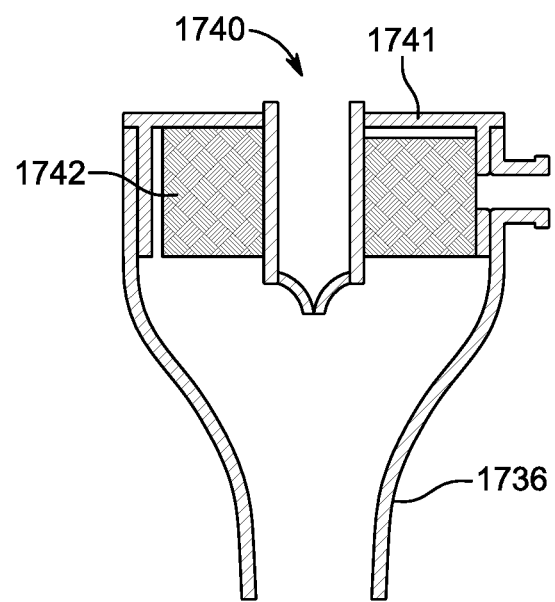
Figure 17C:
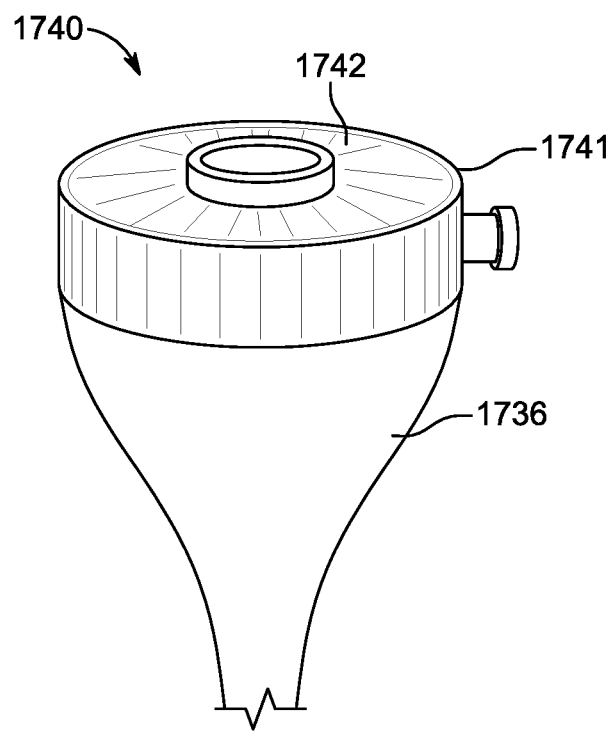
FIG. 17C is a side view of the filter assembly of FIGS. 17A-17B.

Reference is now made to FIGS. 17A to 17C, which are different views of the filter assembly of FIG. 12, constructed and operative in accordance with a further embodiment of the present invention.

FIGS. 17A-17C illustrate a filter assembly 1740 integrated within a patient interface 1736. FIG. 17A shows a patient interface 1736 comprising a main body and a cover 1741 configured to fit into openings of the main body. FIG. 17B shows the same patient interface 1736 in a situation where the cover 1741 is coupled to the main body. In this exemplary embodiment, the cover 1741 may be configured to receive a filter medium 1742.

The patient interface 1736 may be connected to a patient conduit and/or Luer connector. In such embodiment, the patient conduit comprises heating elements (e.g. heater wires) configured to heat humidified gases. The humidified gases may be heated at a temperature higher than a dew point temperature. In other words, the humidified gases are conditioned in a state that compensates for heat losses associated with the parts of the Luer connector and patient interface that are not heated and therefore condensation in the filter assembly 1740 is prevented.

Figure 18:
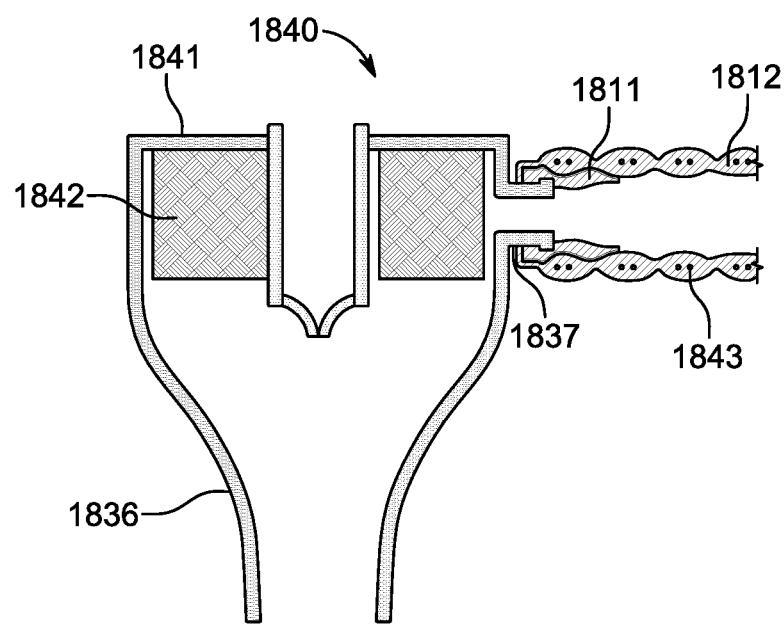
FIG. 18 is a cross sectional view of the filter assembly of FIG. 12, constructed and operative in accordance with an embodiment of the invention.

Reference is now made to FIG. 18, which is a cross sectional view of the filter assembly of FIG. 12, constructed and operative in accordance with an embodiment of the present invention.

FIG. 18 illustrates a filter assembly 1840 similar to the one described in relation to FIGS. 17A-17C. The patient interface 1836 may comprise a main body and a cover 1841 arranged to receive a filter medium 1842. The patient interface 1836 may further comprise a patient interface fitting 1837 configured to be coupled to a patient conduit 1812 via a Luer connector 1811. The patient conduit 1812 may comprise heating elements 1843 (e.g. heater wire) adapted to heat humidified gases flowing through the conduit from the humidifier and also provide radiant heat to the patient interface 1836 and the filter medium 1842.

In such embodiment, at least a portion of the main body and/or at least a portion of the cover 1841 may be made of a thermoconductive plastic material. Similarly, at least a portion of the Luer connector may be made of a thermoconductive material. The heating elements 1843 of the patient conduit 1812 may be arranged so that heat is conducted to the filter medium 1842 via the Luer connector 1811 and the patient interface 1836 so as to prevent and/or reduce condensation in the filter assembly 1840.

Figure 19:
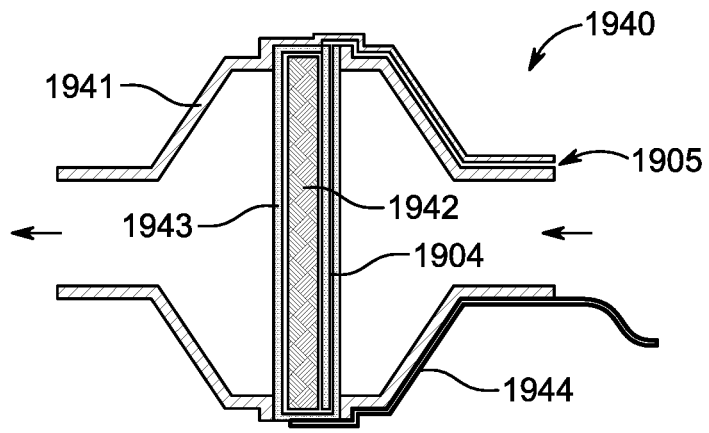
FIG. 19 is a cross sectional view of a filter assembly, constructed and operative in accordance with another embodiment of the invention.

Reference is now made to FIG. 19, which is a cross sectional view of a filter assembly, constructed and operative in accordance with another embodiment of the present invention.

FIG. 19 shows a filter assembly 1940 comprising a housing 1941 and a humidifier 1904 provided as a single unit. Water enters through the gap 1905 and is spread using hydrophilic material positioned adjacent to the filter medium 1942. The entire assembly (i.e. filter assembly 1940 and humidifier 1904) may be heated using a thermally conductive plastic element 1943 surrounding the filter medium 1942 and hydrophilic material and connected to a heating power supply 1944. Gaps in the thermally conductive plastic element 1943 allow gases to flow through the entire assembly and become conditioned in the process. This particular configuration of the filter assembly 1940 and humidifier 1904 is efficient in that little energy is used to heat a small layer of water on the hydrophilic material and little energy is lost by the conditioned gas as it passes through the filter assembly 1940 as the filter medium 1943 is heated by the thermoconductive plastic material element 1943.

Figure 20B:
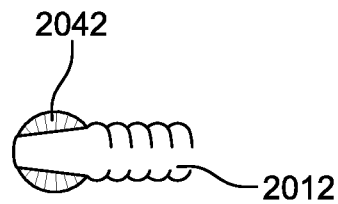
FIG. 20B is a top view of the filter assembly of FIG. 20A.
Figure 20A:
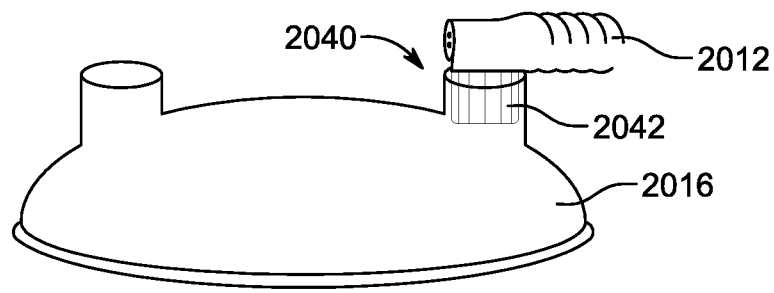
FIG. 20A is a cross sectional view of a filter assembly, constructed and operative in accordance with a further embodiment of the invention.

Reference is now made to FIGS. 20A and 20B, which are different views of a filter assembly, constructed and operative in accordance with a further embodiment of the present invention.

FIGS. 20A and 20B show a filter assembly 2040 provided as part of an elbow connector configured to couple a patient conduit 2012 to the outlet of a humidification chamber 2016. This exemplary embodiment is similar to the one described in relation to FIGS. 9 and 10. However, the filter medium 2042 is coupled to the elbow connector—so as to be within or protruding from the housing 2041—and is configured to be inserted directly into the outlet of the humidification chamber 2016.

Figure 21:
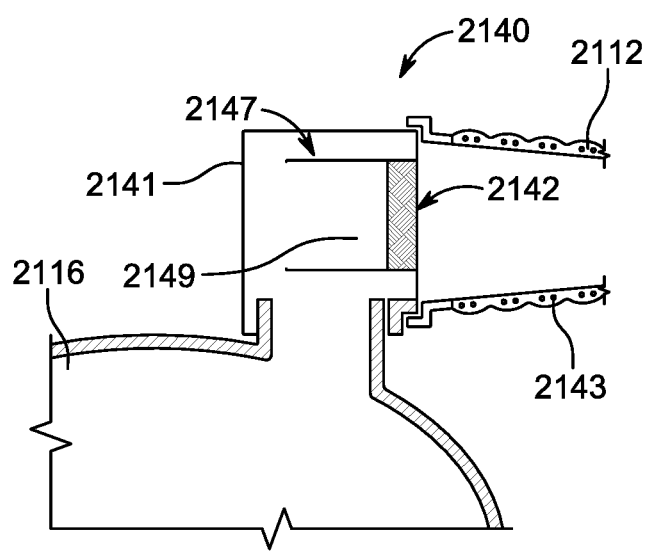
FIG. 21 is a cross sectional view of a filter assembly, constructed and operative in accordance with an embodiment of the invention.

Reference is now made to FIG. 21, which is a cross sectional view of a filter assembly, constructed and operative with an embodiment of the present invention.

FIG. 21 shows a filter assembly 2140 disposed in use between a humidification chamber 2116 and a patient conduit 2112. The filter assembly 2140 comprises a housing 2141 consisting of an air gap 2147 which surrounds the filter medium 2142. The housing 2141 and/or the air gap 2147 is/are configured such that the humidified gases received from the humidifier chamber 2116 enter the air gap 2147 prior to the air gap 2149 where the filter medium 2142 is positioned. With such configuration, the air gap 2149 may be insulated by the humidified gases flowing through the air gap 2147 and therefore heat transfer may be in the direction of the filter medium 2142.

Figure 22A:
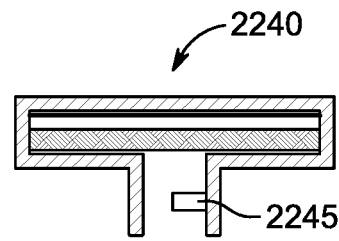
FIGS. 22A-22C are cross sectional views of filter assemblies including a sensor, constructed and operative with further embodiments of the invention.
Figure 22B:
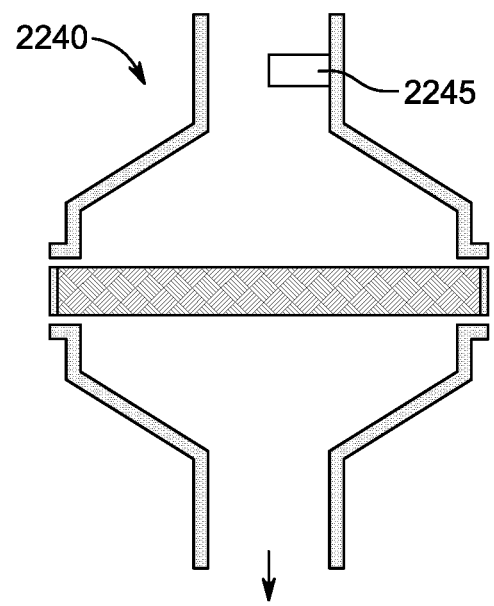
Figure 22C:
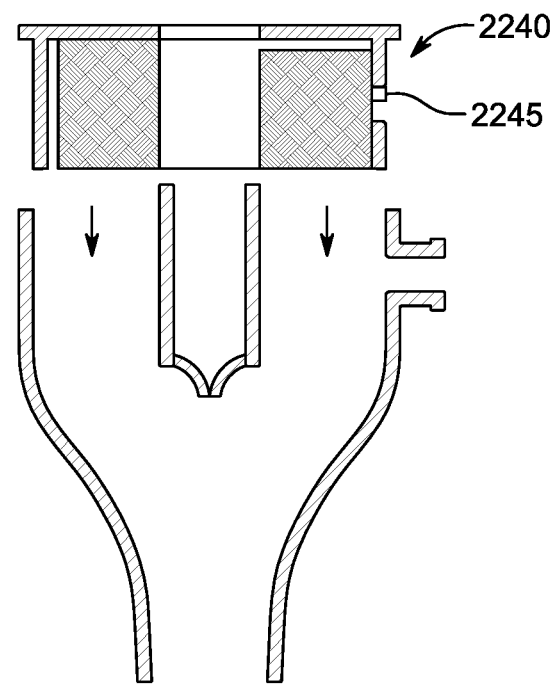

Reference is now made to FIGS. 22A to 22C which are cross sectional views of filter assemblies including a sensor, constructed and operative in accordance with further embodiments of the present invention.

FIGS. 22A to 22C illustrate a filter assembly 2240 that may comprise a sensor 2245. The sensor 2245 may be positioned in the gases flow path at any suitable location. FIG. 22A shows the filter assembly of FIGS. 7A-7B with the sensor 2245 positioned in the inlet port. Similarly, FIG. 22B shows the filter assembly of FIG. 5 with the sensor 2245 being positioned in the inlet port. Lastly, FIG. 22C shows the filter assembly of FIGS. 17A-17C with the sensor 2245 positioned on a side surface of the cover. The sensor 2245 may be configured to measure one or more operating parameter related to the gases flow such as, for example, but not limited to, a temperature, a pressure, humidity and/or a flow rate of the gases. Alternatively, a plurality of sensors may be provided and disposed in the gases flow path and within the filter assembly 2240.

The sensor 2245 may be further configured to transmit the measured data to the humidifier for instance and/or to any other local or remote component of the insufflation system. The measured data may be transmitted by any suitable means such as, for example, but not limited to, a wire associated with the patient conduit (e.g. inside the inner tubing, between the inner and outer tubings, on the outside of the outer tubing, or embedded within either the inner or outer tubings), in a flying lead, or wirelessly using RFID (Radio-Frequency Identification) or Wi-Fi technologies, etc. Non-limiting examples of how the data may be used include: using the measured temperature and/or humidity data in closed loop control of the humidifier; using the measured flow rate and/or pressure data to display the actual pressure drop from the gases source to the patient interface; using the measured flow rate and/or pressure data in closed loop control of the gases source if such control input is available, etc.

Although FIGS. 22A-22C show the filter assemblies depicted in FIGS. 5, 7A-7B and 17A-17C, those skilled in the art will appreciate that sensor 2245 may be used with any of the filter assemblies described hereinabove in relation to FIGS. 1-21.

Figure 23A:
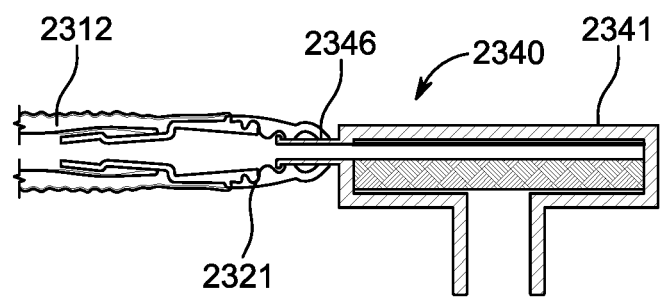
FIGS. 23A and 23B are cross sectional views of filter assemblies, constructed and operative in accordance with embodiments of the invention.
Figure 23B:
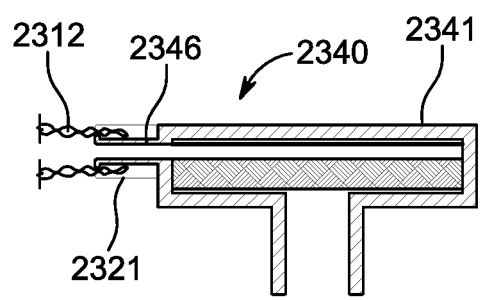

Reference is now made to FIGS. 23A and 23B, which are cross sectional views of a filter assembly, constructed and operative in accordance with an embodiment of the present invention.

FIGS. 23A and 23B show a filter assembly 2340 comprising a filter assembly fitting 2346 on the housing 2341. The filter assembly fitting 2346 may be configured to be coupled to a patient conduit 2312. As it is apparent from FIGS. 23A-23B, a Luer connector 2321 may be provided to couple the filter assembly fitting 2346 to the patient conduit 2312. Those skilled in the art will appreciate that such Luer connector may be used with any suitable filter assembly described hereinabove such as, for example, but not limited to, the filter assemblies shown in FIGS. 1 to 7B.

The Luer connector 2321 of FIG. 23A may comprise a deformable end adjacent to the filter assembly 2340. To connect the filter assembly 2340 to the patient conduit 2312, the filter assembly fitting 2346 is press-fitted into the deformable end of the Luer connector 2321. When the filter assembly fitting 2346 is inserted into the Luer connector 2321, threads on an outer surface of the filter assembly fitting 2346 are configured to grip onto ridges provided in an inner surface of the deformable end of the Luer connector 2321 so as to secure and seal the connection between the Luer connector 2321 and the filter assembly 2340. On the tubing end of the Luer connector 2321, barb and boss connectors may be provided so as to couple the double tubing patient conduit 2312 to the Luer connector 2321.

FIG. 23B shows a filter assembly 2340 similar to the one depicted on FIG. 23A. The Luer connector 2321 is different but is also operative to secure and seal the connection between the Luer connector 2321 and the filter assembly 2340. On the tubing end of the Luer connector 2321, the patient conduit 2312 may be coupled to the Luer connector 2321 by overmoulding for instance.

Figure 24:
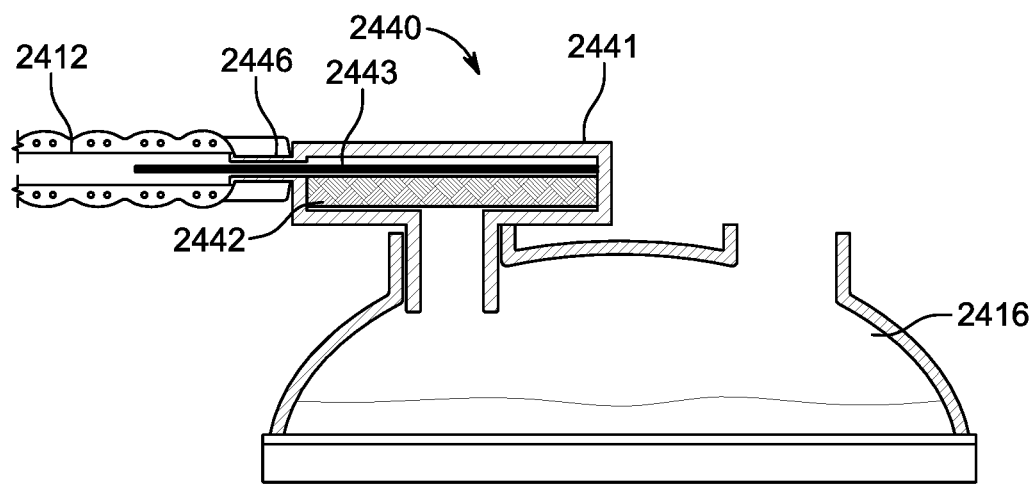
FIG. 24 is a cross sectional view of a filter assembly, constructed and operative in accordance with another embodiment of the invention.

Reference is now made to FIG. 24, which is a cross sectional view of a filter assembly, constructed and operative with another embodiment of the present invention.

The filter assembly 2440 of FIG. 24 comprises a housing 2441, a filter medium 2442 and heating elements 2443. The housing 2441 comprises an inlet operative to be coupled to an outlet port 2418 of the humidification chamber 2416. The filter assembly 2440 is configured so that humidified gases exiting the humidification chamber 2416 enter the filter assembly 2440 at the inlet, pass through the filter medium 2442 and exit the filter assembly 2440 at the outlet 2446 to enter into the patient conduit 2412. As it is apparent from FIG. 24, the humidified gases change direction after the filter medium 2442 to exit the filter assembly 2440 at the outlet 2446. The filter medium 2442 is positioned in use above the outlet port of the humidification chamber 2416. Such configuration improves the reduction in condensation in the filter assembly 2440 as the condensate forming on a surface of the filter medium 2442 facing the humidification chamber 2416 can drain back into the humidification chamber 2416. Additionally, such configuration minimizes the distance between the heating element 2443 and the surface of the liquid present in the humidification chamber 2416 (i.e. the portion of the system during which the humidified gases are not heated) and therefore minimizes condensation in the filter assembly 2440.

Figure 25:
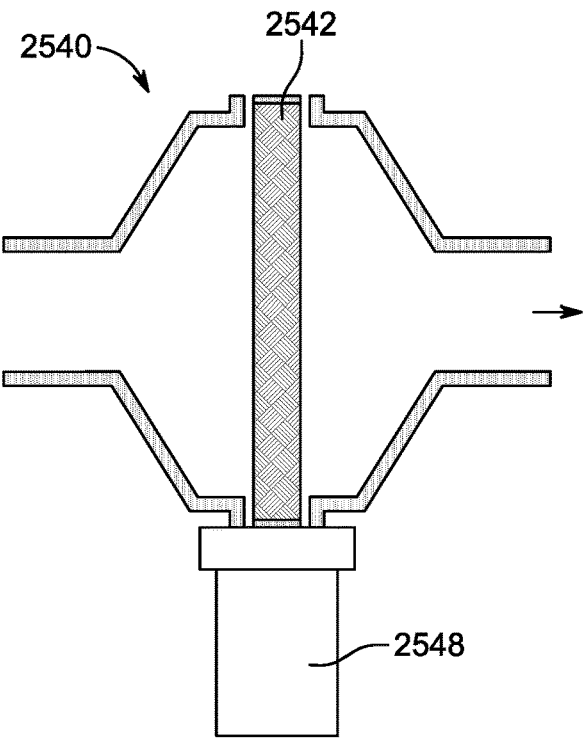
FIG. 25 is a cross sectional view of a filter assembly including a water trap, constructed and operative in accordance with a further embodiment of the invention.

Reference is now made to FIG. 25, which is a cross sectional view filter assembly including a water trap, constructed and operative in accordance with a further embodiment of the present invention.

FIG. 25 shows a filter assembly 2540 similar to the one depicted in FIG. 5. The filter assembly 2540 may further comprise a water trap 2547. The water trap 2647 is positioned below the filter medium 2542 so that condensation forming on a surface of the filter medium 2542 can drain back to the water trap 2547. Those skilled in the art will appreciate that the water trap 2547 may be positioned at any suitable location and/or may be coupled to any suitable element so that condensation forming on a surface of the filter medium 2542 can be received into the water trap 2547.

In addition, those skilled in the art will appreciate that water trap 2547 may be used with any suitable filter assembly described hereinabove in relation to FIGS. 1-24.

Figure 26:
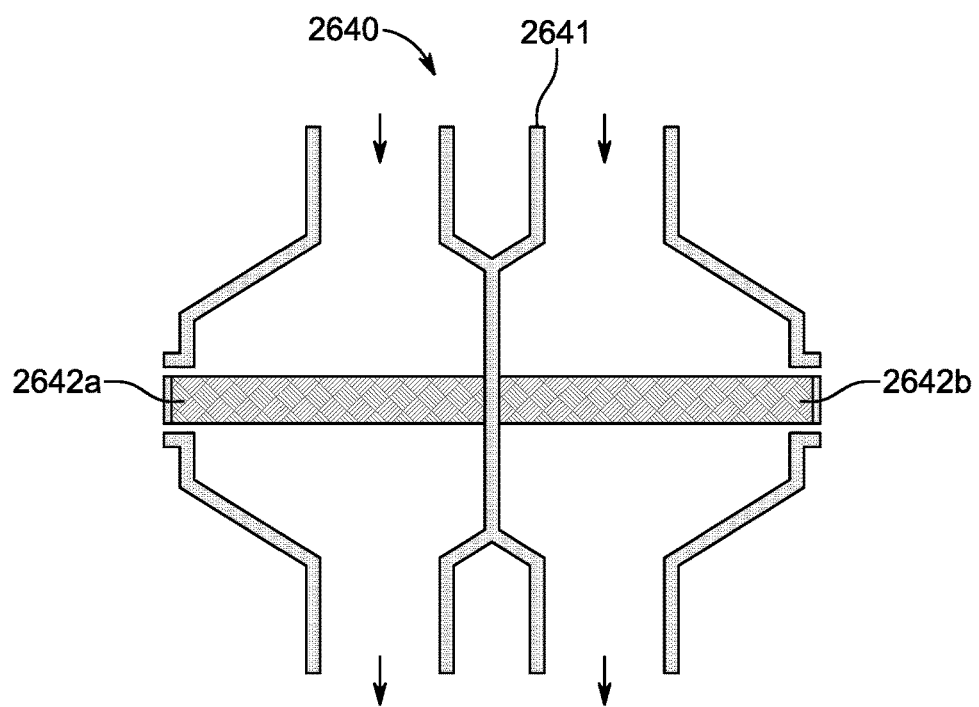
FIG. 26 is a cross sectional view of a filter assembly, constructed and operative in accordance with an embodiment of the invention.

Reference is now made to FIG. 26, which is a cross sectional view of a filter assembly, constructed and operative in accordance with an embodiment of the present invention.

The filter assembly 2640 of FIG. 26 may comprise two lumens. The housing 2641 of the filter assembly 2640 may comprises lumens, each of the lumens comprising an inlet port, an outlet port and a filter medium 2642a, 2642b positioned in use in the gases flow path. Those skilled in the art will appreciate that filter assembly 2640 may comprise any suitable number of lumens and may be used with any suitable filter assembly described hereinabove in relation to FIGS. 1-25.

Figure 27:
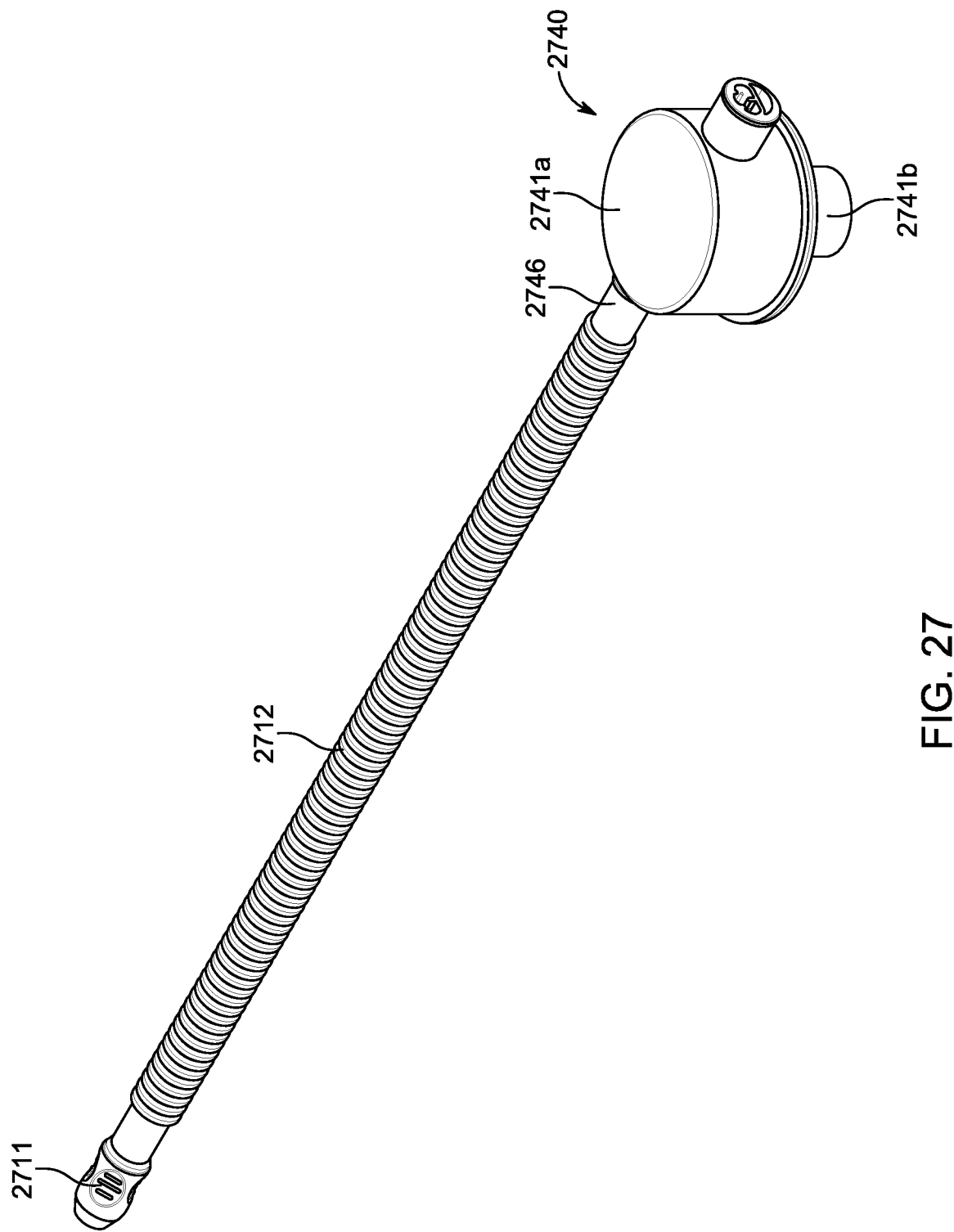
FIG. 27 is an isometric view of a filter assembly, constructed and operative in accordance with another embodiment of the invention.
Figure 28:
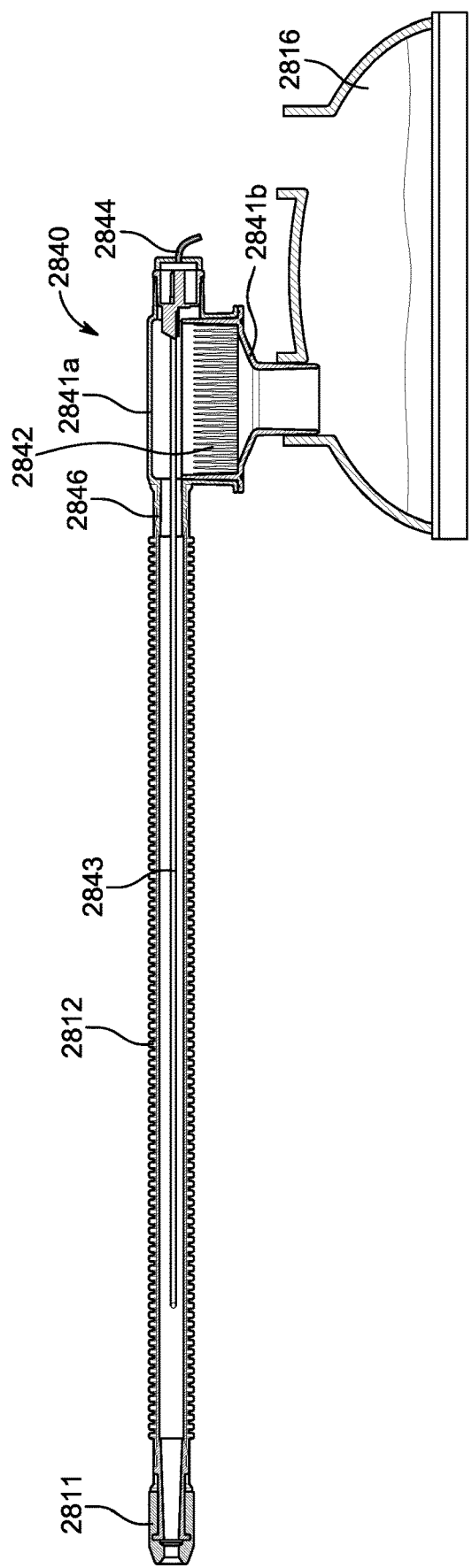
FIG. 28 is a cross sectional view of the filter assembly of FIG. 27.

Reference is now made to FIGS. 27 and 28, which are isometric and cross sectional views of a filter assembly, constructed and operative with another embodiment of the present invention. FIGS. 27 and 28 show a filter assembly 2740, 2840 positioned in use adjacent to the humidifier between the outlet of the humidification chamber 2816 and the patient conduit 2712, 2812. The filter assembly 2740, 2840 comprises a housing 2741a, 2741b, 2841a, 2841b, a filter medium 2842 and heating elements 2843, 2844. The housing may comprise upper 2741a, 2841a and lower 2741b, 2841b portions. The lower portion 2741b, 2841b may comprise an inlet configured to be coupled to an outlet of the humidification chamber 2816 while the upper portion 2741a and 2841a may comprise an outlet 2746, 2846 configured to be coupled to the patient conduit 2712, 2812. In addition, the filter medium 2842 may be disposed in use on the upper portion 2741a, 2841a between the inlet and the outlet 2746, 2846 so that humidified gases entering the lower portion 2841a, 2841b of the housing at the inlet pass through the filter medium 2842 before exiting the upper portion 2741a, 2841a of the housing at the outlet 2746, 2846.

FIG. 28 shows the heating elements 2843, 2844 in greater details. The heating elements may comprise a heater wire 2843 positioned in an upper region of the upper portion 2841a of the housing but spaced apart from the inner top surface. The heater wire 2843 may be the heater wire of the patient conduit 2812 or a separate heater wire configured to extend through and provide additional heating to at least a portion of the patient conduit 2812. In addition, the heater wire 2843 extends through the upper portion 2841a of the housing and is configured to be coupled to an electrical connector 2844 providing power to the heater wire 2843. When the heater wire 2843 is heated by receiving power from the electrical connector 2844, the gases in the filter assembly 2840 and the patient conduit 2812 are therefore heated.

As it is apparent from FIG. 28, the humidified gases change direction after the filter medium 2842 to exit the filter assembly 2840 at the outlet 2846. The filter medium 2842 is positioned in use above the outlet port of the humidification chamber 2816. Such configuration improves the reduction in condensation in the filter assembly 2840 as any condensate forming on a surface of the filter medium 2842 facing the humidification chamber 2816 can drain back into the humidification chamber 2816. Additionally, such configuration minimizes the distance between the heater wire 2843 and the surface of the liquid present in the humidification chamber 2816 (i.e. the portion of the system during which the humidified gases are not heated) and therefore minimizes condensation in the filter assembly 2840.

FIGS. 27 and 28 show a patient conduit 2712, 2812 being coupled, at one end, to the outlet 2746, 2846 of the upper portion 2741a, 2841a of the filter assembly 2740, 2840 and, at another end, to a Luer lock connector 2711, 2811. The Luer connector 2711, 2811 and the outlet 2746, 2846 of the filter assembly 2740, 2840 may be attached to any suitable dual-tubing conduit or any suitable type of single tubing conduit such as, for example, but not limited to: a conduit having annular corrugations as disclosed in U.S. Patent Application No. 2013/0098360 (Fisher & Paykel Limited); a conduit having helical crested corrugations; a conduit having helical corrugations as disclosed in U.S. Patent Application No. 2013/0233318 (Fisher & Paykel Limited); a conduit having an helical bead and bubbles as disclosed in PCT Patent Application WO 2015/142192 (Fisher & Paykel Limited); and a conduit having an helical bead and a film as disclosed in PCT Patent Application WO 2016/048172 (Fisher & Paykel Limited). The patient conduit 2712, 2812 may have an inner tubing, and an outer tubing. The inner tubing provides for a lumen or gases pathway, to allow for the passage of gases along and through the tube. The inner tubing may pneumatically seal with a barb portion provided on a first end of the Luer lock connector 2711, 2811 and/or the outlet 2746, 2846 of the upper portion 2741a, 2841a of the filter assembly 270, 2840. The seal between the inner tubing and the barb portion may be formed by one or more of: deformation of the inner tube around the barb portion, or an adhesive, or an overmould. The outer tubing is located outward or external to the inner tubing. The outer tubing may pneumatically seal with a boss portion provided on the first end of the Luer lock connector 2711, 2811 and/or the outlet 2746, 2846 of the upper portion 2741a, 2841a of the filter assembly 270, 2840. The seal between the outer tubing and the boss portion may be formed by one or more of: deformation of the inner tube around the barb portion, or an adhesive, or an overmould. In some embodiments, the barb portion may act as a stop or surface to engage with an end of the inner tubing to prevent over insertion of the barb portion within the inner tubing. Similarly, in some embodiments a part of the Luer lock connector 2711, 2811 and/or a part of the outlet 2746, 2846 of the upper portion 2741a, 2841a of the filter assembly 270, 2840 may act as a stop for the outer tubing (for example a cuff at the end of the outer tubing).

The inner tubing and outer tubing may provide for a space therebetween. The space may define an insulation layer. The insulation layer may comprise an air gap to insulate the inner tubing with respect to the surrounding environment. The patient conduit 2712, 2812 may also include a heater wire configured to heat the gases in the conduit 2712, 2812. The heater wire may be located in the lumen of the inner tube (e.g. heater wire 2843 also configured to heat the filter medium 2842 of the filter assembly 2841 and/or a separate heater wire), and/or located in or on a wall of the inner tube.

FIGS. 27 and 28 also show the patient conduit 2712, 2812 being coupled to a Luer lock connector 2711, 2811. The Luer lock connector may comprise a body having an interior region defining a gases flow passageway allowing insufflation/humidified gases to flow through. The body can comprise a first end that removably connects to a fitting of a patient interface (e.g. patient interface 136 of FIG. 1) and a second end that permanently attaches to the tubing of the patient conduit 2712, 2812. It will be appreciated that the Luer lock connector 2711, 2811 can be a high flow Luer lock connector providing particular sealing and retention features with less resistance to gases flow than traditional Luer connectors of the art. Embodiments of such high flow Luer lock connectors 2711, 2811 are described, for example, in International Patent Application No. PCT/NZ2017/050149 (Fisher & Paykel Limited), which is incorporated by reference herein in its entirety.

There have been described and illustrated herein several embodiments of a filter assembly. While particular embodiments of the invention have been described, it is not intended that the invention be limited thereto, as it is intended that the invention be as broad in scope as the art will allow and that the specification be read likewise. Thus, while particular types of housing, heating element and filter medium have been disclosed, it will be appreciated that any suitable combination of these may be used to provide a filter assembly. In addition, while particular types of materials, sensors, connectors, tubings, water traps and lumens have been disclosed, it will be understood that other types can be used. It will therefore be appreciated by those skilled in the art that yet other modifications could be made to the provided invention without deviating from its spirit and scope as claimed.

What is claimed is:

1. A filter assembly for use in an insufflation system, said filter assembly being positioned, in use, between a humidification apparatus and a patient, said filter assembly comprising:
   a filter medium operative to filter medical gases;
   a housing comprising an inlet, an outlet and said filter medium, said housing defining a gases flow path for directing the medical gases from said inlet, through said filter medium, and out said outlet to the patient; and
   at least one heating element positioned at least partially within said housing and configured to heat said filter medium, wherein said at least one heating element comprises one or more heater wires;
   wherein, within said housing, said at least one heating element is spaced apart from said filter medium and from an inner surface of said housing, and wherein said at least one heating element is at least partially suspended within said housing,
   wherein said at least one heating element is positioned in said gases flow path downstream from said filter medium, and
   wherein said at least one heating element is configured to extend through said outlet of said housing so as to be positionable within a patient conduit connected to said outlet of said housing.

2. The filter assembly of claim 1, wherein said outlet of said housing is configured to be coupled to the patient conduit, and wherein said patient conduit is configured to deliver said medical gases passing through said filter assembly to the patient.

3. The filter assembly of claim 2, wherein said patient conduit is permanently attached to said outlet.

4. The filter assembly of claim 2, wherein said patient conduit is removably attached to said outlet.

5. The filter assembly of claim 2, wherein said at least one heating element is configured to extend along a length of said patient conduit.

6. The filter assembly of claim 2, wherein said patient conduit comprises heating wires configured to heat said medical gases flowing through said patient conduit.

7. The filter assembly of claim 6, wherein said heating wires are attached to or comprise said at least one heating element of said filter assembly.

8. The filter assembly of claim 1, wherein said filter assembly further comprises an electrical power source coupling configured to supply power to said at least one heating element.

9. The filter assembly of claim 1, wherein said filter assembly is sterile.

10. The filter assembly of claim 1, wherein said filter medium comprises one or more of the following: a membrane, a glass-based material, a hydrophilic material, paper, and a pleated material.

11. The filter assembly of claim 1, wherein said filter assembly further comprises at least one sensor positioned in said gases flow path between said inlet and said outlet of said housing, wherein said sensor is configured to measure data indicative of one or more of the following: a temperature; a humidity; a pressure; and a flow rate of said gases flow.

12. The filter assembly of claim 1, wherein said inlet of said housing is configured to be coupled to a humidification chamber.

13. The filter assembly of claim 1, wherein said housing comprises an electrical connector configured to provide an electrical connection to said at least one heating element.

14. The filter assembly of claim 1, wherein said insufflation system comprises the humidification apparatus operative to humidify said medical gases for delivery to a patient, and wherein said filter assembly is positioned in use between said humidification apparatus and said patient.

15. The filter assembly of claim 14, wherein said filter assembly is positioned in use adjacent to a humidification chamber of said humidification apparatus.

16. The filter assembly of claim 1, wherein said at least one heating element is positioned in said gases flow path between said inlet and said outlet of said housing.

17. A filter assembly for use in an insufflation system, said filter assembly being positioned, in use, between a humidification apparatus and a patient, said filter assembly comprising:
a filter medium operative to filter medical gases;
a housing comprising an inlet, an outlet and said filter medium, said housing defining a gases flow path for directing the medical gases from said inlet, through said filter medium, and out said outlet to the patient; and
at least one heating element positioned at least partially within said housing and configured to heat said filter medium;
wherein, within said housing, said at least one heating element is spaced apart from said filter medium and from an inner surface of said housing, and wherein said at least one heating element is at least partially suspended within said housing,
wherein said at least one heating element is positioned in said gases flow path downstream from said filter medium,
wherein said at least one heating element is configured to extend through said outlet of said housing so as to be positionable within a patient conduit connected to said outlet of said housing, and
wherein said filter assembly further comprises at least one sensor positioned in said gases flow path between said inlet and said outlet of said housing, wherein said sensor is configured to measure data indicative of one or more of the following: a temperature; a humidity; a pressure; and a flow rate of said gases flow.

18. The filter assembly of claim 17, wherein said filter assembly is positioned in use adjacent to a humidification chamber of said humidification apparatus.

19. The filter assembly of claim 17, wherein said at least one heating element is positioned in said gases flow path between said inlet and said outlet of said housing.

\* \* \* \* \*